United States Patent
Onozuka et al.

(10) Patent No.: US 10,744,311 B2
(45) Date of Patent: Aug. 18, 2020

(54) MICRONEEDLE UNIT AND INJECTION DEVICE

(71) Applicant: ASTI CORPORATION, Hamamatsu-shi, Shizuoka (JP)

(72) Inventors: Kenpei Onozuka, Hamamatsu (JP); Noriyuki Ogai, Hamamatsu (JP)

(73) Assignee: ASTI CORPORATION, Hamamatsu-Shi, Shizuoka (JP)

( * ) Notice: Subject to any disclaimer, the term of this patent is extended or adjusted under 35 U.S.C. 154(b) by 377 days.

(21) Appl. No.: 15/113,282

(22) PCT Filed: Jan. 28, 2015

(86) PCT No.: PCT/JP2015/052300
§ 371 (c)(1),
(2) Date: Jul. 21, 2016

(87) PCT Pub. No.: WO2015/115455
PCT Pub. Date: Aug. 6, 2015

(65) Prior Publication Data
US 2017/0007812 A1 Jan. 12, 2017

(30) Foreign Application Priority Data
Jan. 29, 2014 (JP) ................................ 2014-013850

(51) Int. Cl.
*A61M 37/00* (2006.01)

(52) U.S. Cl.
CPC ... *A61M 37/0015* (2013.01); *A61M 2037/003* (2013.01); *A61M 2037/0023* (2013.01); *A61M 2202/30* (2013.01)

(58) Field of Classification Search
CPC ...... A61M 37/0015; A61M 2037/0023; A61M 2037/003; A61M 2005/004;
(Continued)

(56) References Cited

U.S. PATENT DOCUMENTS

| | | | | |
|---|---|---|---|---|
| 3,072,122 A | * | 1/1963 | Rosenthal | ........................ 604/46 |
| 5,314,412 A | * | 5/1994 | Rex | ............................... 604/191 |
| 7,344,499 B1 | * | 3/2008 | Prausnitz | ........... A61M 37/0015 |
| | | | | 600/309 |

FOREIGN PATENT DOCUMENTS

| | | | | |
|---|---|---|---|---|
| JP | 2005-527249 A | | 9/2005 | |
| JP | 2005246595 A | * | 9/2005 | ........ A61M 37/0015 |

(Continued)

OTHER PUBLICATIONS

Machine translation of JP 2008154849; Sugiyama; translated by https://worldwide.espacenet.com/ on Aug. 6, 2018.*
(Continued)

*Primary Examiner* — Nathan R Price
*Assistant Examiner* — Melissa A Snyder
(74) *Attorney, Agent, or Firm* — Manabu Kanesaka

(57) ABSTRACT

The purpose of the present invention is to provide a micro-needle unit and an injection device capable of being readily connected to a liquid supply source and capable of performing an effective injection via a simple configuration. The micro-needle unit is provided with a plurality of micro-needles disposed on the puncturing side and provided with a flow channel, and drug solution supply needles disposed on the side opposite from the puncturing side in a number less than that of the micro-needles and provided with a flow channel in communication with the aforementioned flow channel, the micro-needle unit thereby being capable of being readily connected to a liquid supply source and capable of performing an effective injection via a simple configuration.

25 Claims, 13 Drawing Sheets

(58) Field of Classification Search
CPC .... A61M 5/1407; A61M 5/284; A61M 5/285; A61M 2005/2013; A61M 2037/0038; A61M 37/0084; A61M 5/162; A61M 39/14; A61M 3/005; A61M 5/2448
See application file for complete search history.

(56) References Cited

FOREIGN PATENT DOCUMENTS

| JP | 2008-154849 | A |   | 7/2008 |            |
|----|-------------|---|---|--------|------------|
| JP | 2008154849  | A | * | 7/2008 | A61M 37/0015 |
| JP | 2009-532117 | A |   | 9/2009 |            |
| JP | 2011083484  | A | * | 4/2011 | A61M 37/0015 |
| JP | 2012-010735 | A |   | 1/2012 |            |
| JP | 2013-90977  | A |   | 5/2012 |            |
| JP | 2012-157406 | A |   | 8/2012 |            |

OTHER PUBLICATIONS

PCT/ISA/210, "International Search Report for International Application No. PCT/JP2015/052300," dated Apr. 28, 2015.

* cited by examiner

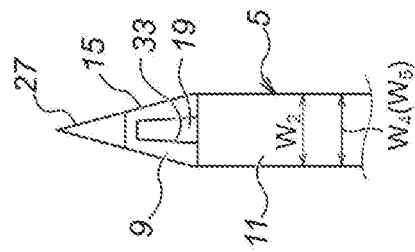
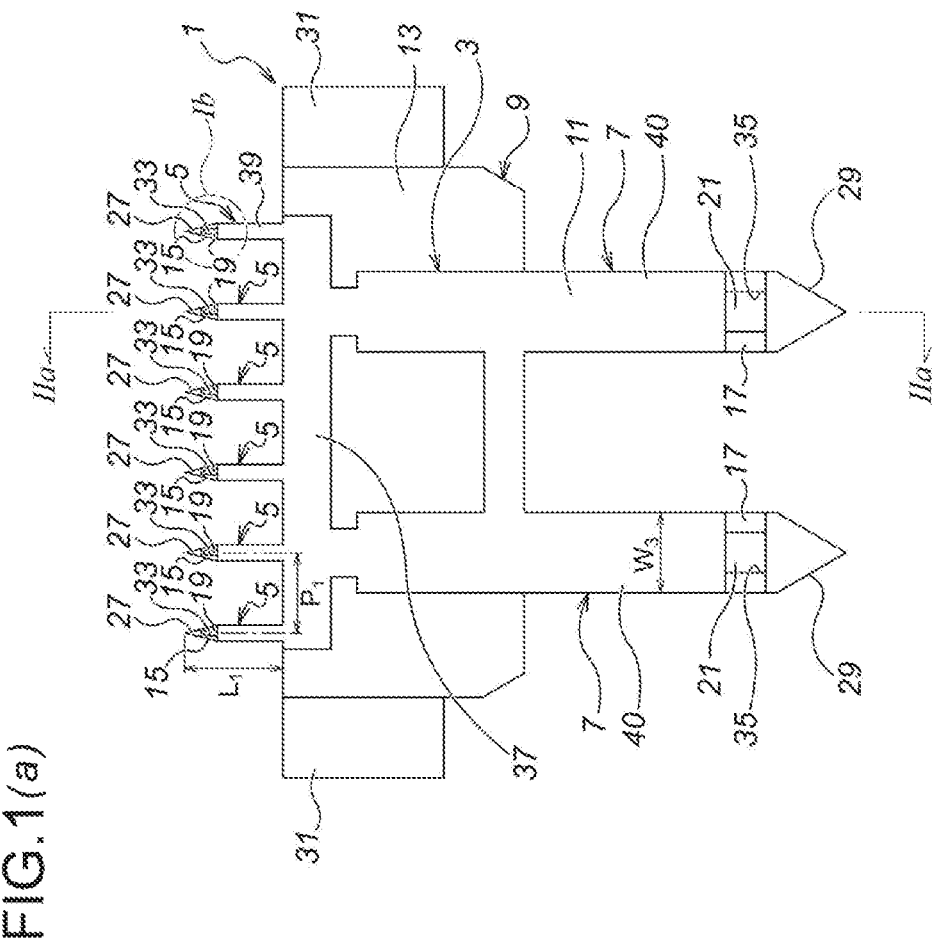

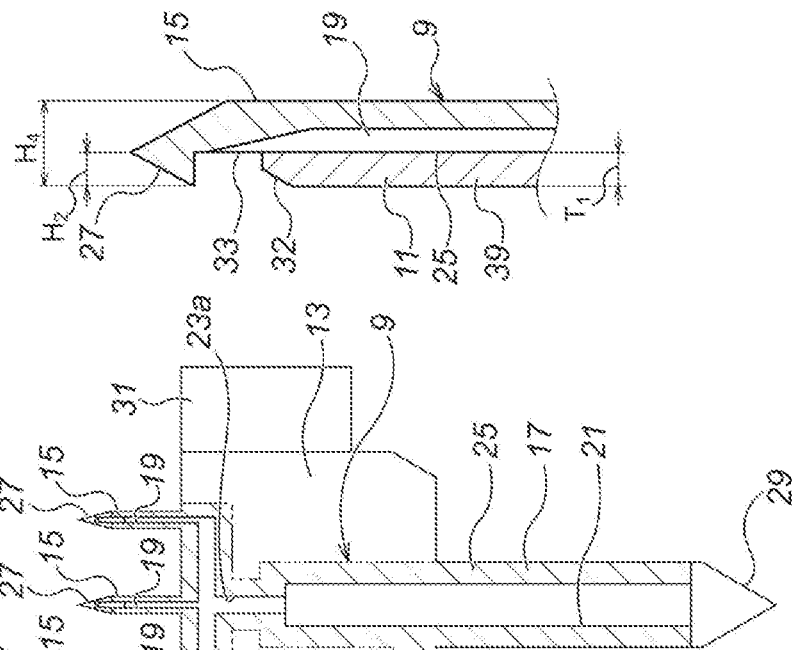
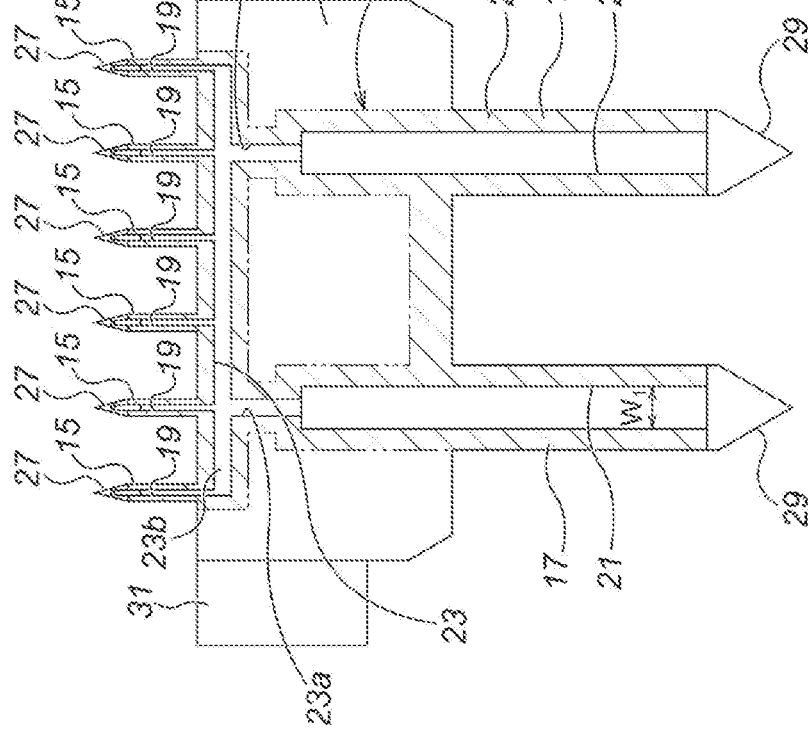
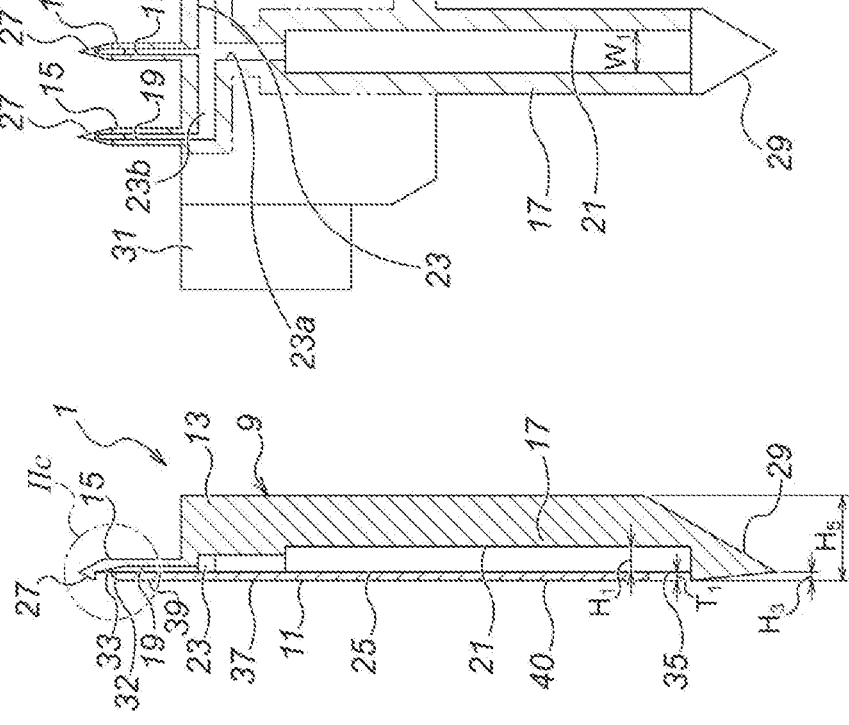

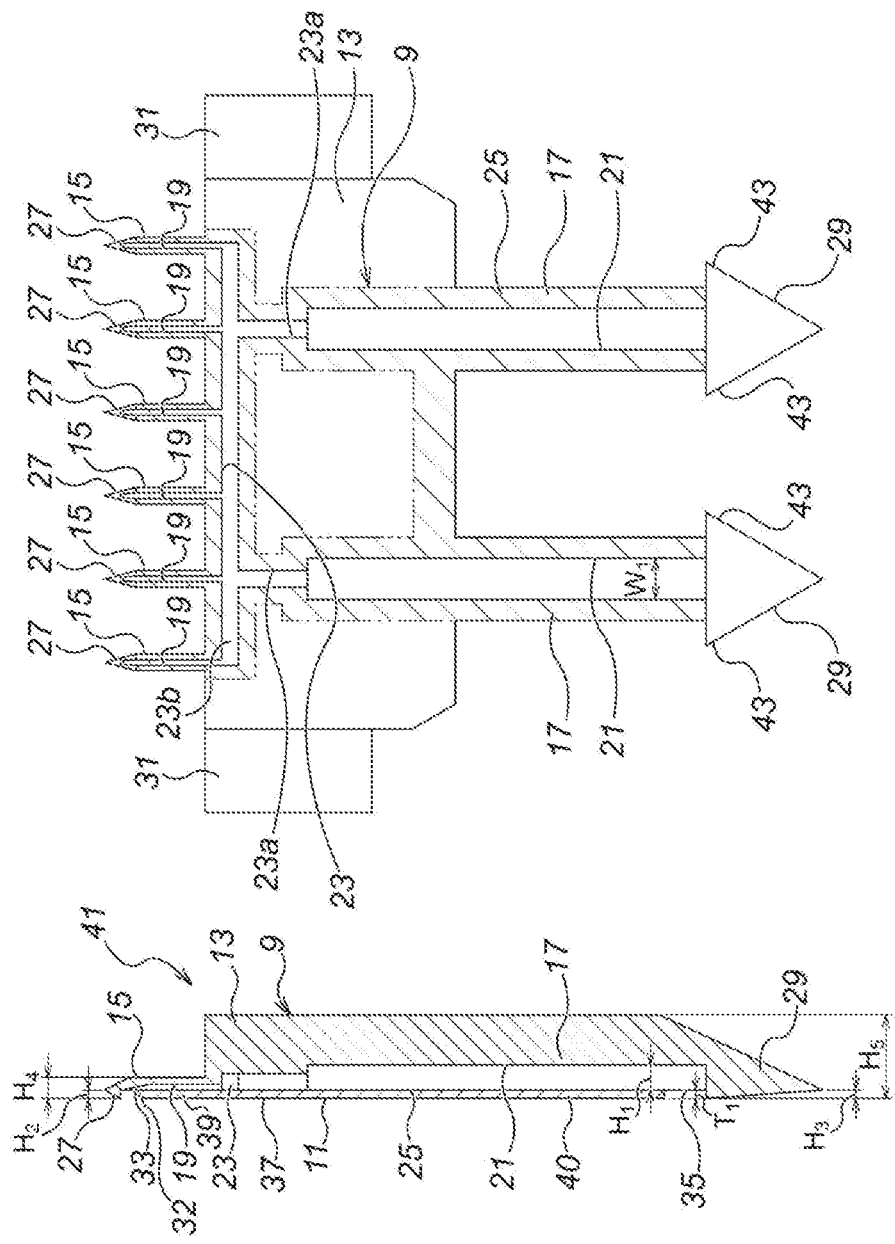

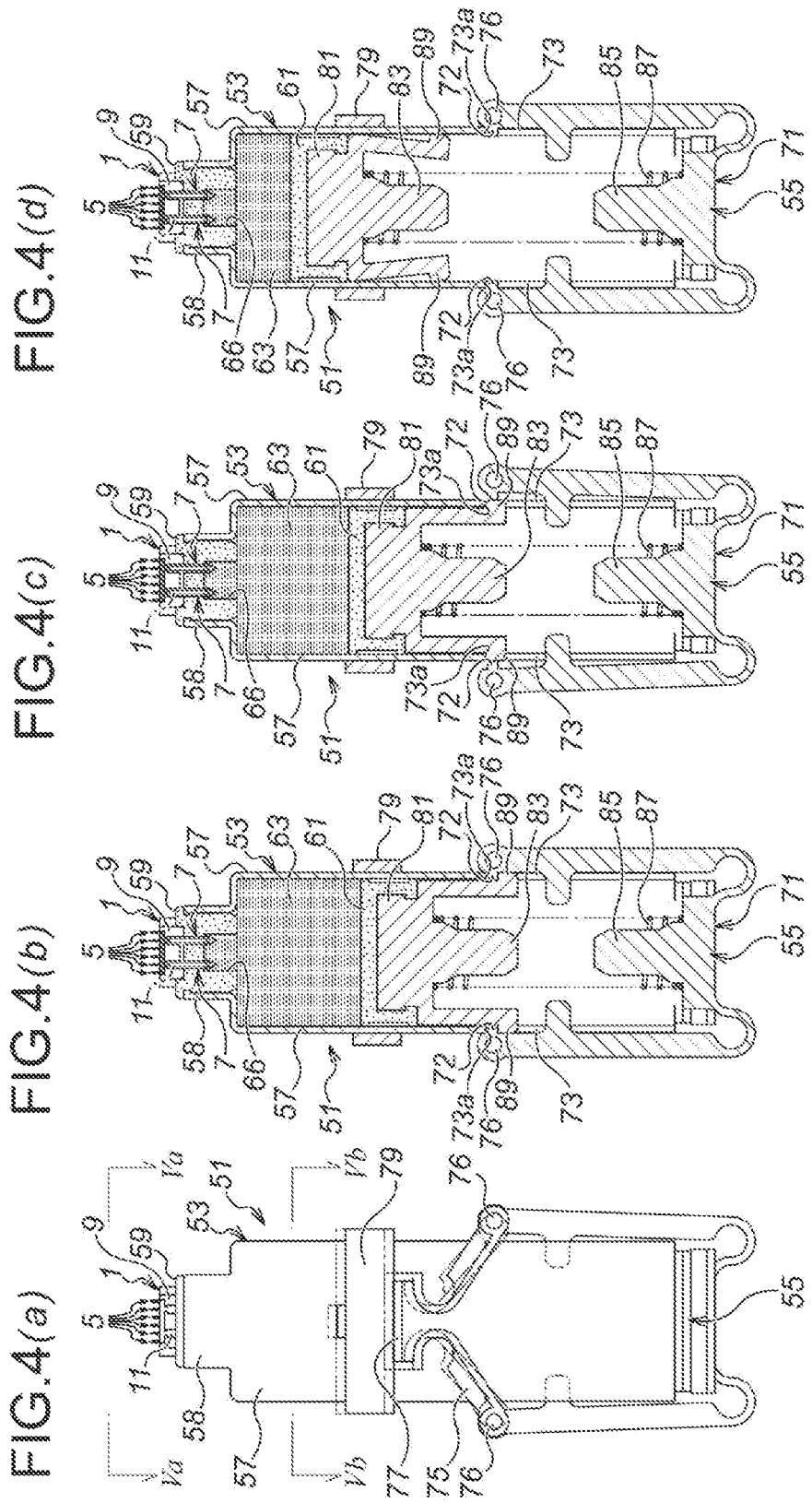

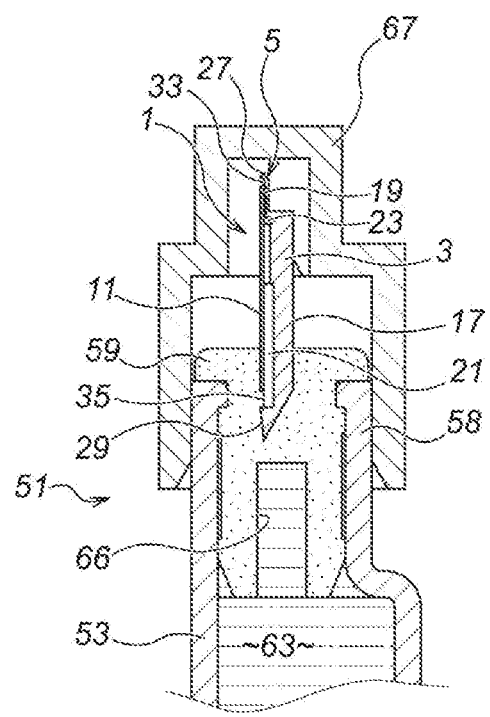
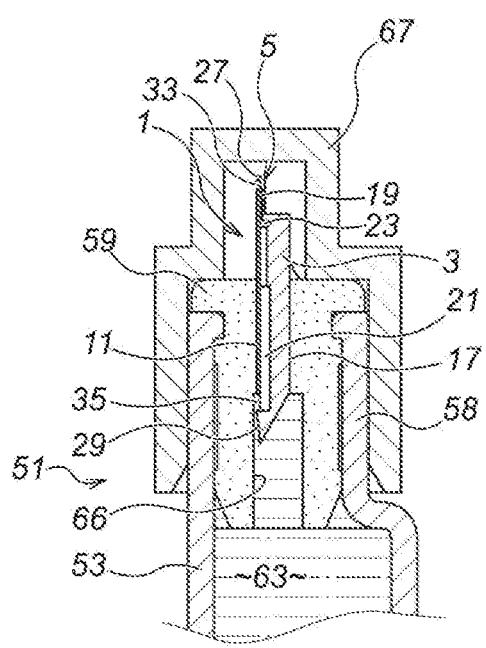

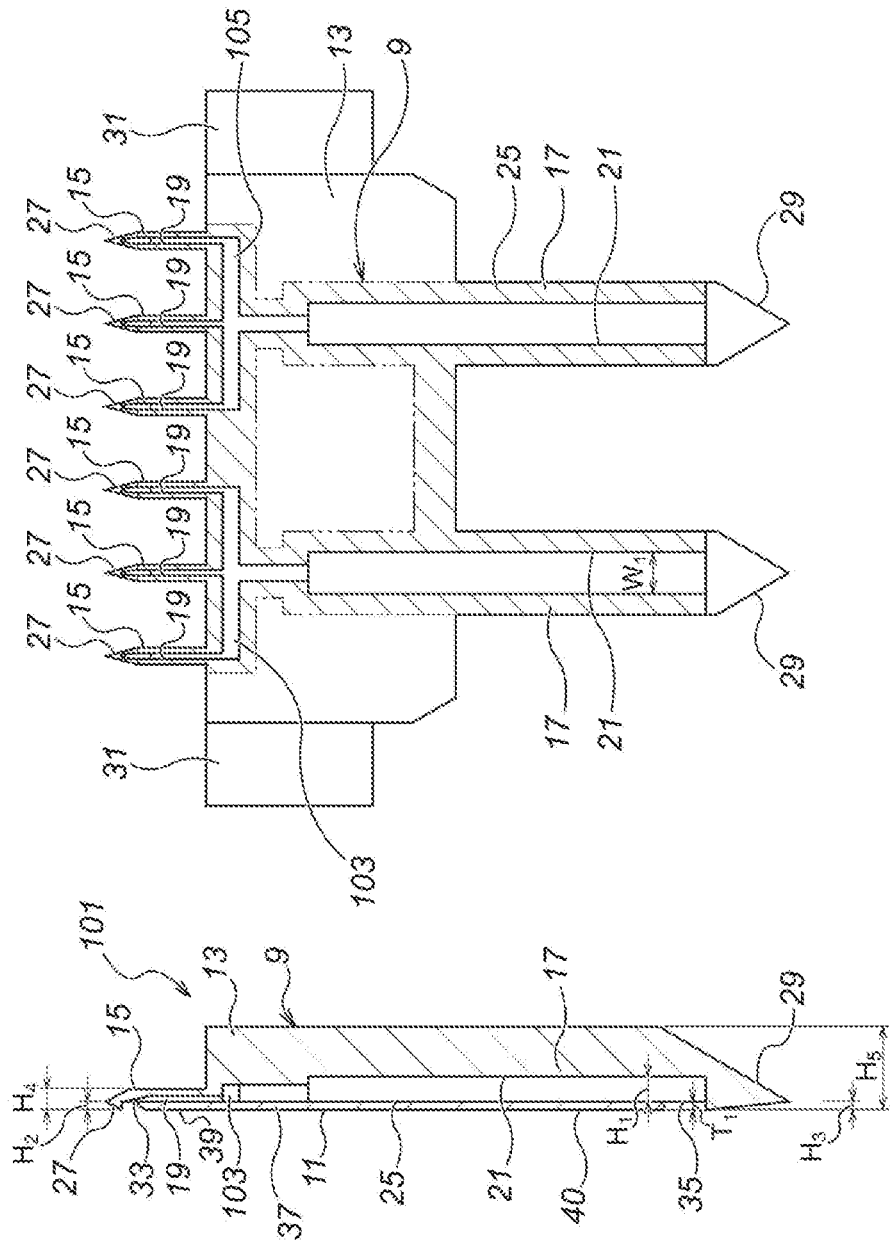

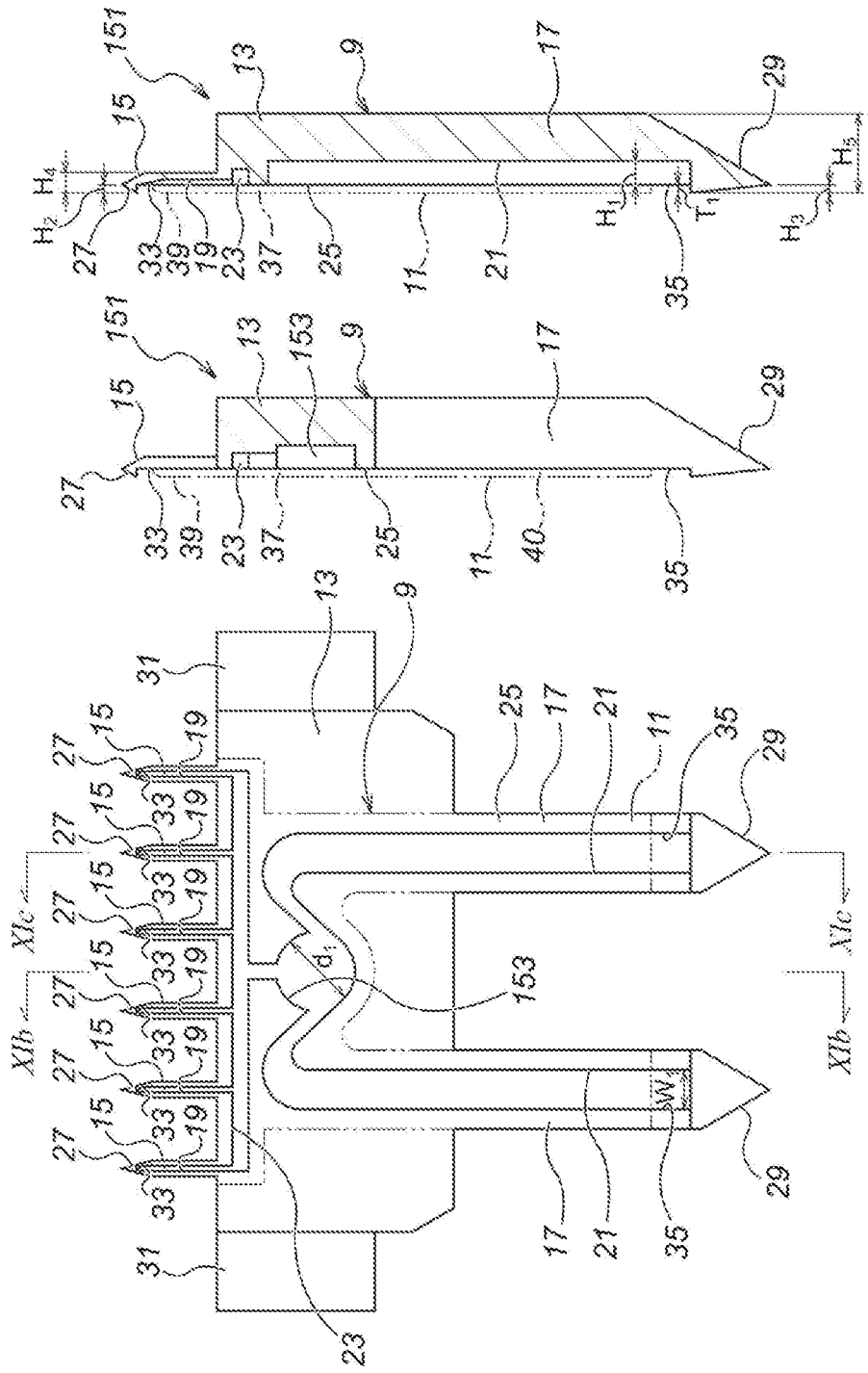

MICRONEEDLE UNIT AND INJECTION DEVICE

RELATED APPLICATIONS

The present application is National Phase of International Application No. PCT/JP2015/052300 filed Jan. 28, 2015, and claims priority from Japanese Application No. 2014-013850, filed Jan. 29, 2014, the disclosure of which is hereby incorporated by reference herein in its entirety.

TECHNICAL FIELD

The present invention relates to a microneedle unit for performing prevention and treatment of various diseases, for example by subcutaneous or intracutaneous administration of an objective substance such as medicinal agent (hereinafter referred to as "objective substance"), and an injection device in which such an microneedle unit is incorporated, and more specifically, relates to that, of which connection is facilitated by simplifying the structure on the side of supplying medicinal solution, and also that, which can perform injection by supplying the medicinal solution effectively in a desired broad area.

BACKGROUND ART

A microneedle device provided with fine needles (microneedles) is effective as a less-invasive percutaneous medicinal solution delivery device. However, since the microneedle has a fine needle structure, the manufacturing and handling thereof is difficult as compared with a conventional injection needle.

In particular, with regard to a hollow-shaped microneedle having a flow channel formed therein likewise the structure of the conventional injection needle, because of its fine structure, the manufacturing thereof is difficult, and further, the connection thereof with solution delivery means for delivering a medicinal solution to be injected, such as a syringe, a tube or a pump, is also difficult.

Therefore, the applicant of the present invention has filed a patent application for a jig for microneedle array placement and a microneedle array device as disclosed in Patent Document 1, of which structure will be explained briefly as below:

First, there is a plurality of microneedle units provided with a plurality of microneedles, respectively, and this plurality of microneedle units is integrated by a needle holder (for example, made of rubber), and is accommodated in a case comprising an upper case and a lower case. With regard to the microneedle unit, flow channel bosses formed in the microneedle unit are inserted with pressure into medicinal solution distribution holes formed in the needle holder, so as to be connected to the needle holder.

Moreover, a medicinal solution inlet is formed in the lower case, and the medicinal solution inlet is communicating with the flow channels of the all microneedle units. Thus, a medicinal solution inlet is connected, via a tube, etc., to a pump, etc., and the medicinal solution is supplied, via the tube and the medicinal solution inlet, to the microneedle units, and eventually to the microneedles.

Moreover, there are other inventions as disclosed in Patent Document 2 and Patent Document 3.

With regard to a medicinal solution container and a medicinal solution injection device as described in Patent Document 2, a needle tube having needles at the both ends (double-headed needle) is provided, and one end of the needle tube penetrates a seal member to be immersed in a medicinal solution container filled with a medicinal solution, and the other end of the needle tube discharges the medicinal solution into the skin. As compared with the structure of Patent Document 1, the structure of Patent Document 2 has a simpler structure with a less number of component parts, and since the needle tube penetrates the seal member to be immersed in the medicinal solution container, the risk of leakage of medicinal solution is low.

Moreover, with regard to a pre-filled syringe as described in Patent Document 3, a double-headed needle is provided similarly, so that one end of the double-headed needle penetrates a seal body to be immersed in the medicinal solution container, and the other end of the double-headed needle discharges the medicinal solution into the skin. Also in this case, as compared with the structure of Patent Document 1, the structure is simpler with a less number of component parts, and since the one end of the double-headed needle penetrates the seal body to be immersed in the medicinal solution container, the risk of leakage of medicinal solution is low.

REFERENCE DOCUMENTS OF CONVENTIONAL ART

Patent Document(s)

Patent Document 1: International Publication WO 2012/057270 A1.
Patent Document 2: Official Gazette, JP 2012-10971 A.
Patent Document 3: Official Gazette, JP 2011-212183 A.

SUMMARY OF THE INVENTION

Problems to be Solved by Invention

However, the above structures of the prior arts have the following problems:

First, in the case of the jig for microneedle array placement as described in Patent Document 1, the structure on the side of supplying the medicinal solution into the microneedles is complicated, and moreover, the number of component parts will become larger.

Moreover, it is difficult to secure the preciseness between the flow channel boss of the microneedle unit and the medicinal solution flow channel of the needle holder to be inserted with pressure, which will increase the risk of leakage of medicinal solution.

Moreover, although the microneedle unit is provided with a plurality of microneedles, since each microneedle punctures a different position of the skin having different surface hardness and evenness, it is difficult to perform a uniform puncturing into the skin by every microneedle, and there is a problem of leakage of medicinal solution out of some of the microneedles.

Moreover, with regard to the medicinal solution container and the medicinal solution injection device of Patent Document 2 and the pre-filled syringe of Patent Document 3, although the structure on the side of supplying the medicinal solution is simplified by using the double-headed needle, since this is composed of a single needle, it is impossible to perform injection in a desired broad area, and for example, it is impossible to cause immune cells to take in the medicinal solution efficiently.

Moreover, in general, when a painless puncturing is intended, the diameter of needle should be reduced, but because of the single-needle structure as described above, the injection volume of medicinal solution is limited by reduction of the diameter, and there is a problem that a desired volume of medicinal solution cannot be injected.

To cope with this problem, it is possible to increase the injection area by providing a plurality of the double-headed needles, but this structure increases the number of component parts, and in addition, it is difficult to provide the all double-headed needles with a uniform depth of puncturing.

In the light of the above problems, it is an object of the present invention to provide a microneedle unit and an injection device, of which connection is facilitated by simplifying the structure on the side of supplying the medicinal solution, and which can perform injection by supplying the medicinal solution effectively in a desired broad area.

Means to Solve the Problem

To achieve the objects mentioned above, a microneedle unit according to first aspect of the present invention is comprising: a plurality of microneedles disposed on a puncturing side and provided with flow channels; and medicinal solution supply needles disposed on a counter-puncturing side in a number less than the number of the microneedles, provided with flow channels communicating to the flow channels of the microneedles.

Moreover, the microneedle unit according to second aspect is characterized in that, with reference to the microneedle unit of first aspect, the flow channels of the microneedles are consolidated into the flow channels of the medicinal solution supply needles.

Moreover, the microneedle unit according to third aspect is characterized in that, with reference to the microneedle unit of first aspect or second aspect, characterized in that, the medicinal solution supply needles are provided in a plural number, and the flow channels of the plurality of medicinal solution supply needles confluent into a communication path, to communicate with the flow channels of the microneedles via the communication path.

Moreover, the microneedle unit according to fourth aspect is characterized in that, with reference to the microneedle unit of any one of first aspect to third aspect, the size of the flow channels becomes smaller gradually from the medicinal solution supply needle toward the microneedle.

Moreover, the microneedle unit according to fifth aspect is characterized in that, with reference to the microneedle unit of any one of first aspect to fourth aspect, the microneedles and/or the medicinal solution supply needles are composed of two divisional elements bonded with each other.

Moreover, the microneedle unit according to sixth aspect is characterized in that, with reference to the microneedle unit of fifth aspect, one divisional element of two of the divisional elements is provided with arrowhead parts on the top end side.

Moreover, the microneedle unit according to seventh aspect is characterized in that, with reference to the microneedle unit of fifth aspect or sixth aspect, an outlet is formed at the top end of the microneedle, and the outlet is a downwardly-opening hole, a horizontally-opening hole, or an upwardly-opening hole.

Moreover, the microneedle unit according to eighth aspect is characterized in that, with reference to the microneedle unit of sixth aspect, barb parts are provided at the top end on a medicinal solution supply side of the one divisional element.

Moreover, the microneedle unit according to ninth aspect is characterized in that, with reference to the microneedle unit of sixth aspect or eighth aspect, the lower surface of a section of the one divisional element constituting a part of the microneedle is flat.

Moreover, the microneedle unit according to tenth aspect is characterized in that, with reference to the microneedle unit of any one of fifth aspect to ninth aspect, a bonding surface of two of the divisional elements is flat.

Moreover, the microneedle unit according to eleventh aspect is characterized in that, with reference to the microneedle unit of any one of fifth aspect to tenth aspect, at least one of two of the divisional elements is made by molding of a resin material.

Moreover, the microneedle unit according to twelfth aspect is characterized in that, with reference to the microneedle unit of sixth aspect or eighth aspect or ninth aspect, the thickness of another divisional element of two of the divisional elements is set not to be larger than the height of the arrowhead part protruding from a divisional surface of the one divisional element.

Moreover, the microneedle unit according to thirteenth aspect is characterized in that, with reference to the microneedle unit of sixth aspect or eighth aspect or ninth aspect or tenth aspect or eleventh aspect, a chamfered part is formed on the top end side of the microneedle of the other divisional element of two of the divisional elements.

Moreover, the microneedle unit according to fourteenth aspect is characterized in that, with reference to the microneedle unit of twelfth aspect or thirteenth aspect, a section of the other divisional element of two of the divisional elements constituting a part of the microneedle is flat.

Moreover, the microneedle unit according to fifteenth aspect is characterized in that, with reference to the microneedle unit of any one of twelfth aspect to fourteenth aspect, the other divisional element is in a form of a film, a sheet or a tape.

Moreover, the microneedle unit according to sixteenth aspect is characterized in that, with reference to the microneedle unit of any one of twelfth aspect to fifteenth aspect, the external dimensions of the other divisional element is slightly smaller than the external dimensions of the one divisional element.

Moreover, the microneedle unit according to seventieth aspect is characterized in that, with reference to the microneedle unit of any one of first aspect to sixteenth aspect, the medicinal solution supply needles are provided in a plural number, and the plurality of microneedles is sorted into groups so that the microneedles of each group and one medicinal solution supply needle of the plurality of medicinal solution supply needles constitute one set, and the flow channels are compartmented by each of the sets.

Moreover, the microneedle unit according to eighteenth aspect is characterized in that, with reference to the microneedle unit of any one of first aspect to sixteenth aspect, the medicinal solution supply needles are provided in a plural number, and the flow channels of the plurality of medicinal solution supply needles are consolidated into one mixing chamber, and the mixing chamber is communicating with the flow channels of the plurality of microneedles.

Moreover, an injection device according to nineteenth aspect is characterized in that: the microneedle unit as claimed in any one of first aspect to eighteenth aspect is set; and the injection device is in a flattened shape expanding in the alignment direction of the microneedles of the microneedle unit.

Moreover, the injection device unit according to twentieth aspect is characterized in that, with reference to the injection device unit of nineteenth aspect, the microneedles are set so as to offset from the center of the injection device.

Moreover, the injection device unit according to twenty first aspect is characterized in that, with reference to the injection device of nineteenth aspect or twentieth aspect: a medicinal solution retaining part sealed by a seal member is provided; and, with the penetration of the medicinal solution supply needles through the seal member, a medicinal solution in the medicinal solution retaining part is delivered to the microneedles via the medicinal solution supply needles.

Moreover, the injection device unit according to twenty second aspect is characterized in that, with reference to the injection device of any one of nineteenth aspect to twenty first aspect: the microneedles are covered with a needle cap; and, with the depressing of the needle cap, the medicinal solution supply needles penetrate through the seal member.

Moreover, the injection device unit according to twenty third aspect is characterized in that, with reference to the injection device of twenty first aspect, a depressing mechanism is provided so as to extract the air from the medicinal solution retaining part.

Moreover, the injection device unit according to twenty fourth aspect is characterized in that, with reference to the injection device of twenty third aspect: a locking mechanism is provided so as to lock the depressing mechanism; and, with the release of the locking mechanism, the depressing mechanism discharges the medicinal solution from the outlets of the microneedles.

Moreover, the injection device unit according to twenty fifth aspect is characterized in that, with reference to the injection device of twenty first aspect or twenty third aspect, the medicinal solution retaining parts are provided in a plural number.

Moreover, the injection device unit according to twenty sixth aspect is characterized in that, with reference to the injection device of twenty fifth aspect: the microneedle unit as claimed in seventieth aspect is set; a different types of medicinal solutions are retained, respectively, in the plurality of medicinal solution retaining parts; and the plurality of medicinal solution supply needles corresponds to the plurality of medicinal solution retaining parts.

Moreover, the injection device unit according to twenty seventh aspect is characterized in that, with reference to the injection device of twenty fifth aspect: the microneedle unit as claimed in eighteenth aspect is set; a different types of medicinal solutions are retained, respectively, in the plurality of medicinal solution retaining parts; and the plurality of medicinal solution supply needles corresponds to the plurality of medicinal solution retaining parts.

Effect of the Invention

As discussed above, the microneedle unit of first aspect is comprising: a plurality of microneedles disposed on a puncturing side and provided with flow channels; and medicinal solution supply needles disposed on a counter-puncturing side in a number less than the number of the microneedles, provided with flow channels communicating to the flow channels of the microneedles. Therefore, the structure on the side of the medicinal solution supply can be simplified, and moreover, it is possible to connect to the side of the medicinal solution supply easily, and moreover, it is possible to perform injection by supplying the medicinal solution in a desired broad area.

Moreover, according to the microneedle unit of second aspect, with reference to the microneedle unit of first aspect, the flow channels of the microneedles are consolidated into the flow channels of the medicinal solution supply needles. Therefore, the medicinal solution can be delivered uniformly to each of the microneedles.

Moreover, according to the microneedle unit of third aspect, with reference to the microneedle unit of first aspect or second aspect, the medicinal solution supply needles are provided in a plural number, and the flow channels of the plurality of medicinal solution supply needles confluent into a communication path, to communicate with the flow channels of the microneedles via the communication path. Therefore, when different types of medicinal solutions are delivered separately from each of the medicinal solution supply needles, it is possible to mix them so as to deliver to the microneedles.

Moreover, according to the microneedle unit of fourth aspect, with reference to the microneedle unit of any one of first aspect to third aspect, the size of the flow channels becomes smaller gradually from the medicinal solution supply needle toward the microneedle. Therefore, the resistance the flow channel resistance can be reduced, and it is possible to perform injection by the microneedles smoothly.

Moreover, according to the microneedle unit of fifth aspect, with reference to the microneedle unit of any one of first aspect to fourth aspect, the microneedles and/or the medicinal solution supply needles are composed of two divisional elements bonded with each other. Therefore, the manufacturing thereof is easy even in the case that a complicated flow channels are provided in the inside. Moreover, it is possible to increase the freedom of design of shapes of flow channels, etc., and accordingly, it is possible to accomplish the structure easily, in which, the plurality of microneedles and the medicinal solution supply needles in a number less than that of the plurality of microneedles, are provided.

Moreover, according to the microneedle unit of sixth aspect, with reference to the microneedle unit of fifth aspect, one divisional element of two of the divisional elements is provided with arrowhead parts on the top end side. Therefore, the top end side is not in the bonded structure, and therefore, it is possible to secure the sufficient strength of the top end side. Moreover, since the bonding of two divisional elements at the fine top end side is not required, the manufacturing thereof is easy.

Moreover, according to the microneedle unit of seventh aspect, with reference to the microneedle unit of fifth aspect or sixth aspect, an outlet is formed at the top end of the microneedle, and the outlet is a downwardly-opening hole, a horizontally-opening hole, or an upwardly-opening hole. Therefore, during injecting, it is possible to prevent the outlets from being blocked by the skin tissue, and the medicinal solution can be infiltrated into the skin tissue efficiently.

Moreover, according to the microneedle unit of eighth aspect, with reference to the microneedle unit of sixth aspect, barb parts are provided at the top end on a medicinal solution supply side of the one divisional element. Therefore, the microneedles and the medicinal solution supply needles cannot be dropped off easily. Moreover, in the case that the barb parts are provided only on the side of the medicinal solution supply needles, after injecting, when the microneedles are pulled out from an object of puncturing (for example, the skin), since the medicinal solution supply needles are much harder to be pulled out than the microneedles, it is possible to pull out the microneedles securely from the object of puncturing (for example, the skin).

Moreover, according to the microneedle unit of ninth aspect, with reference to the microneedle unit of sixth aspect or eighth aspect, the lower surface of a section of the one divisional element constituting a part of the microneedle is flat. Therefore, it is possible to reduce the resistance during puncturing. Moreover, since the resistance is reduced, it is also possible to prevent separation of the divisional elements during puncturing.

Moreover, according to the microneedle unit of tenth aspect, with reference to the microneedle unit of any one of fifth aspect to ninth aspect, a bonding surface of two of the divisional elements is flat. Therefore, the bonding of the one divisional element with the other divisional element can be performed easily.

Moreover, according to the microneedle unit of eleventh aspect, with reference to the microneedle unit of any one of fifth aspect to tenth aspect, at least one of two of the divisional elements is made by molding of a resin material. Therefore, the cost thereof can be reduced by mass production, and the microneedle unit can be prepared as a disposal type. Moreover, it is possible to increase the freedom of design of the shape of the microneedle unit.

Moreover, according to the microneedle unit of twelfth aspect, with reference to the microneedle unit of sixth aspect or eighth aspect or ninth aspect, the thickness of another divisional element of two of the divisional elements is set not to be larger than the height of the arrowhead part protruding from a divisional surface of the one divisional element. Therefore, during puncturing, it is possible to prevent the other divisional element from being detached.

Moreover, according to the microneedle unit of thirteenth aspect, with reference to the microneedle unit of sixth aspect or eighth aspect or ninth aspect or tenth aspect or eleventh aspect, a chamfered part is formed on the top end side of the microneedle of the other divisional element of two of the divisional elements. Therefore, for example, even in the case that the other divisional element becomes thicker because of molding workability or the thickness of a sheet material, the resistance during puncturing can be reduced. Moreover, since the resistance is reduced, it is also possible to prevent separation of the divisional elements during puncturing.

Moreover, according to the microneedle unit of fourteenth aspect, with reference to the microneedle unit of twelfth aspect or thirteenth aspect, a section of the other divisional element of two of the divisional elements constituting a part of the microneedle is flat. Therefore, it is possible to reduce the resistance during puncturing. Moreover, since the resistance is reduced, it is also possible to prevent separation of the divisional elements during puncturing.

Moreover, according to the microneedle unit of fifteenth aspect, with reference to the microneedle unit of any one of twelfth aspect to fourteenth aspect, the other divisional element is in a form of a film, a sheet or a tape. Therefore, the manufacturing thereof is easy. Moreover, any versatile material in a form of a film, a sheet or a tape can be used. Moreover, the mass production thereof is easy by roll bonding, and further, it is possible to bond the other divisional element with the one divisional element uniformly.

Moreover, according to the microneedle unit of sixteenth aspect, with reference to the microneedle unit of any one of twelfth aspect to fifteenth aspect, the external dimensions of the other divisional element is slightly smaller than the external dimensions of the one divisional element. Therefore, the alignment thereof during bonding is easy, and the mass production thereof is also easy. Moreover, since the other divisional element in a form of a film or a sheet does not protrude toward the outer periphery of the one divisional element, during puncturing, it is possible to prevent the other divisional element from being caught by the object of puncturing (for example, the skin) and being separated from the one divisional element.

Moreover, according to the microneedle unit of seventeenth aspect, with reference to the microneedle unit of any one of first aspect to sixteenth aspect, the medicinal solution supply needles are provided in a plural number, and the plurality of microneedles is sorted into groups so that the microneedles of each group and one medicinal solution supply needle of the plurality of medicinal solution supply needles constitute one set, and the flow channels are compartmented by each of the sets. Therefore, it is possible to perform injection by preventing the different types of medicinal solutions from being mixed. Moreover, with this structure, it is possible to facilitate the handling of different types of medicinal solutions of which mixing is prohibited, and the burden on the user can be relieved.

Moreover, according to the microneedle unit of eighteenth aspect, with reference to the microneedle unit of any one of first aspect to sixteenth aspect, the medicinal solution supply needles are provided in a plural number, and the flow channels of the plurality of medicinal solution supply needles are consolidated into one mixing chamber, and the mixing chamber is communicating with the flow channels of the plurality of microneedles. Therefore, it is possible to perform injection by mixing different types of medicinal solutions. Moreover, since the mixing chamber is provided, the mixing of the different types of medicinal solutions can be performed effectively. Moreover, with this structure, it is possible to facilitate the handling of different types of medicinal solutions to be mixed, and the burden on the user can be relieved.

Moreover, according to an injection device of nineteenth aspect: the microneedle unit as claimed in any one of first aspect to eighteenth aspect is set; and the injection device is in a flattened shape expanding in the alignment direction of the microneedles of the microneedle unit. Therefore, there is no structural element in the direction orthogonal to the alignment direction of the microneedles, and it is possible to perform puncturing easily, in a state that the microneedles are inclined in a direction orthogonal to the alignment direction of the microneedles. Accordingly, during puncturing, even where the object of puncturing (for example, the skin) is deformed, it is possible to perform puncturing securely. Moreover, even in the case that the depth of puncturing is shallow, the depth of puncturing can be controlled easily.

Moreover, according to the injection device of twentieth aspect, with reference to the injection device unit of nineteenth aspect, the microneedles are set so as to offset from the center of the injection device. Therefore, it is possible to perform injection easily by inclining toward the offset side.

Moreover, according to the injection device of twenty first aspect, with reference to the injection device of nineteenth aspect or twentieth aspect: a medicinal solution retaining part sealed by a seal member is provided; and, with the penetration of the medicinal solution supply needles through the seal member, a medicinal solution in the medicinal solution retaining part is delivered to the microneedles via the medicinal solution supply needles. Therefore, the structure to deliver the medicinal solution to the microneedle unit can be simplified. Moreover, with the seal member, the leakage of the medicinal solution can be prevented securely.

Moreover, according to the injection device of twenty second aspect, with reference to the injection device of any one of nineteenth aspect to twenty first aspect: the microneedles are covered with a needle cap; and, with the depressing of the needle cap, the medicinal solution supply needles penetrate through the seal member. Therefore, it is possible to prevent the microneedles in a non-use state, from being deformed or damaged, or from unintended puncturing. Moreover, via the needle cap, it is possible to become in a state easily, in which the medicinal solution is supplied to the microneedles.

Moreover, according to the injection device of twenty third aspect, with reference to the injection device of twenty first aspect, a depressing mechanism is provided so as to extract the air from the medicinal solution retaining part. Therefore, it is possible to prevent unintended injection of the air. Moreover, with the depressing mechanism, the air can be extracted from the medicinal solution retaining part.

Moreover, according to the injection device of twenty fourth aspect, with reference to the injection device of twenty third aspect: a locking mechanism is provided so as to lock the depressing mechanism; and, with the release of the locking mechanism, the depressing mechanism discharges the medicinal solution from the outlets of the microneedles. Therefore, the medicinal solution can be discharged from the outlets of the microneedles by simple operation.

Moreover, according to the injection device of twenty fifth aspect, with reference to the injection device of twenty first aspect or twenty third aspect, the medicinal solution retaining parts are provided in a plural number. Therefore, it is possible to store a plurality of medicinal solutions in a stable state, of which mixing is prohibited.

Moreover, according to the injection device of twenty sixth aspect, with reference to the injection device of twenty fifth aspect: the microneedle unit as claimed in seventeenth aspect is set; a different types of medicinal solutions are retained, respectively, in the plurality of medicinal solution retaining parts; and the plurality of medicinal solution supply needles corresponds to the plurality of medicinal solution retaining parts. Therefore, it is possible to perform individual injection of the plural types of medicinal solutions easily.

Moreover, according to the injection device of twenty seventh aspect, with reference to the injection device of twenty fifth aspect: the microneedle unit as claimed in claim 18 eighteenth aspect is set; a different types of medicinal solutions are retained, respectively, in the plurality of medicinal solution retaining parts; and the plurality of medicinal solution supply needles corresponds to the plurality of medicinal solution retaining parts. Therefore, immediately before injecting, it is possible to mix the plural types of medicinal solutions easily, and to perform injection.

BRIEF DESCRIPTION OF DRAWINGS

FIG. 1 Drawings showing a first embodiment of the present invention, namely: FIG. 1 (a) is a plan view showing an exterior of a microneedle unit; and FIG. 1 (b) is an expanded view of a section Ib of FIG. 1 (a).

FIG. 2 Drawings showing the first embodiment of the present invention, namely: FIG. 2 (a) is a sectional view as seen from the line IIa-IIa of FIG. 1; FIG. 2 (b) is a plan view of a first divisional element; and FIG. 2 (c) is an expanded view of a section IIc of FIG. 2 (a).

FIG. 3 Drawings showing a second embodiment of the present invention, namely: FIG. 3 (a) is a longitudinal sectional view of a microneedle unit; and FIG. 3 (b) is a plan view of a first divisional element.

FIG. 4 Drawings showing a third embodiment of the present invention, namely: FIG. 4 (a) is a plan view of an injection device; FIG. 4 (b) is a longitudinal plan sectional view of the injection device in a non-injecting state; FIG. 4 (c) is a longitudinal plan sectional view of the injection device in an air discharging state; and FIG. 4 (d) is a longitudinal plan sectional view of the injection device in an injecting state.

FIG. 5 (a) is a view as seen from the arrows Va-Va of FIG. 4 (a); and FIG. 5 (b) is a sectional view as seen from the line Vb-Vb of FIG. 4 (a).

FIG. 6 (a) is a partial longitudinal sectional view showing a state that a seal member of the injection device is not penetrated by a microneedle unit; and FIG. 6 (b) is a partial longitudinal sectional view showing a state that the seal member of the injection device is penetrated by the microneedle unit.

FIG. 7 Drawings showing the third embodiment of the present invention, namely: FIG. 7 (a) is a sectional view as seen from the line VIIa-VIIa of FIG. 6 (a); and FIG. 7 (b) is a sectional view as seen from the line VIIb-VIIb of FIG. 6 (b).

FIG. 8 Drawings showing a fourth embodiment of the present invention, namely: FIG. 8 (a) is a longitudinal sectional view of a microneedle unit according to the present embodiment; and FIG. 8 (b) is a plan view of a first divisional element.

FIG. 9 (a) is a longitudinal plan sectional view of an injection device in a non-injecting state; FIG. 9 (b) is a longitudinal plan sectional view of the injection device in an air discharging state; and FIG. 9 (c) is a longitudinal plan sectional view of the injection device in an injecting state.

FIG. 11 Drawings showing a fifth embodiment of the present invention, namely: FIG. 11 (a) is a plan view of a first divisional element of a microneedle unit; FIG. 11 (b) is a sectional view as seen from the line XIb-XIb of FIG. 11 (a); and FIG. 11 (c) is a sectional view as seen from the line XIc-XIc of FIG. 11 (a).

FIG. 12 (a) is a longitudinal plan sectional view of an injection device in a non-injecting state; FIG. 12 (b) is a longitudinal plan sectional view of the injection device in an air discharging state; and FIG. 12 (c) is a longitudinal plan sectional view of the injection device in an injecting state.

MODE(S) FOR CARRYING OUT THE INVENTION

Figure 5A:
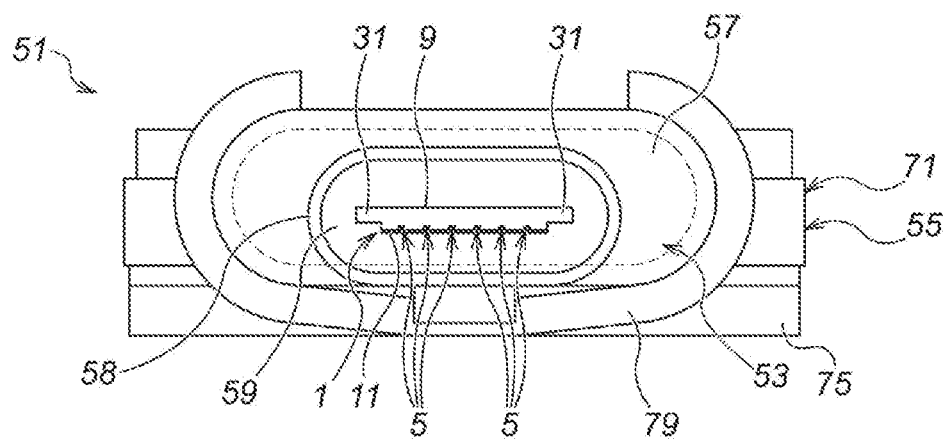
FIG. 5 Drawings showing the third embodiment of the present invention, namely.

A first embodiment of the present invention will be explained as below, with reference to FIG. 1 and FIG. 2.

As illustrated in FIG. 1, a microneedle unit 1 according to the first embodiment is composed of: a unit main body 3 substantially in a plate shape; a plurality of (in the first embodiment, six) microneedles 5 protrusively disposed on one side (on the upper side of FIG. 1 (a)) of the unit main body 3; and a plurality of (in the first embodiment, two)

medicinal solution supply needles 7 protrusively disposed on the other side (on the lower side of FIG. 1 (*a*)) of the unit main body 3.

Moreover, the microneedle unit 1 according to the first embodiment is composed of two divisional elements bonded with each other, namely, a first divisional element 9 and a second divisional element 11 bonded with each other. Moreover, with regard to the microneedle unit 1, the microneedles 5 are provided so as to deviate toward the side of the second divisional element 11 (toward the left side of FIG. 2 (*a*)), namely, so as to offset toward the side of the second divisional element 11 (toward the left side of FIG. 2 (*a*)).

Now the structure of each part will be explained in detail.

First, the structure of the first divisional element 9 is explained. The first divisional element 9 is manufactured, for example, by injection molding of a resin material. Moreover, the first divisional element 9 is made of, for example, versatile plastic such as polycarbonate or polyethylene, or biodegradable plastic such as polylactic acid or polyglycolic acid, and it is preferable to be made of biodegradable plastic from the viewpoint of biosafety.

Moreover, the first divisional element 9 is manufactured by injection molding using an upper mold and a lower mold, and at that time, by considering the freedom of design of the unit main body 3, the microneedles 5 and medicinal solution supply needles 7, the directions of mold removal are set to be orthogonal to the axis directions of the microneedles 5 and the medicinal solution supply needles 7 (for example, in the directions perpendicular to the drawing sheet surface of FIG. 1 (*a*)).

Moreover, with regard to the first divisional element 9, as illustrated in FIG. 2, first, there is a first divisional element main body 13 substantially in a plate shape, and a plurality of (in the first embodiment, six) microneedle part first elements 15 is protrusively disposed on the upper side of the first divisional element main body 13 as seen in FIG. 2 (*b*). Moreover, a plurality of (in the first embodiment, two) medicinal solution supply needle part first elements 17 is protrusively disposed on the lower side of the first divisional element body 13 as seen in FIG. 2 (*b*).

Moreover, a microneedle side flow channel 19 is formed in the microneedle part first element 15. The microneedle side flow channel 19 is provided as a groove, formed to be open toward the front side of the first divisional element 9 as seen in the direction perpendicular to the drawing sheet surface of FIG. 2 (*b*).

Moreover, a medicinal solution supply needle side flow channel 21 is formed in the medicinal solution supply needle part first element 17. The medicinal solution supply needle side flow channel 21 is also provided as a groove, formed to be open toward the front side of the first divisional element 9 as seen in the direction perpendicular to the drawing sheet surface of FIG. 2 (*b*).

Moreover, a communication path 23 is formed in the first divisional element main body 13, for communicating the microneedle side flow channels 19 with the medicinal solution supply needle side flow channels 21. The communication path 23 is also provided as a groove, formed to be open toward the front side of the first divisional element 9 as seen in the direction perpendicular to the drawing sheet surface of FIG. 2 (*b*).

The communication path 23 is composed of communication path elements 23*a*, 23*a* for communicating with the medicinal solution supply needle side flow channels 21, 21, respectively, and a communication path element 23*b* for communicating these communication path elements 23*a*, 23*a* with the six microneedle side flow channels 19 as described above.

Moreover, the width ($W_1$) and the depth ($H_1$) of the medicinal solution supply needle side flow channels 21, the communication path 23 and the microneedle side flow channels 19 are set to become smaller gradually, in the order the medicinal solution supply needle side flow channels 21, the communication path 23 and the microneedle side flow channels 19.

Moreover, as illustrated in FIG. 2 (*b*), a bonding section 25 (a shaded section defined by imaginary lines in FIG. 2 (*b*)) for bonding the first divisional element 9 with the second divisional element 11, on the outer peripheral sides of the microneedle side flow channels 19, the medicinal solution supply needle side flow channels 21 and the communication path 23. Thus, the bonding section 25 is coated with an unillustrated adhesive, whereby the first divisional element 9 and the second divisional element 11 are adhered and fixed to each other.

Note that, in the first embodiment, although the adhering and fixing by using the adhesive is explained as an example, it is also possible to adhere and fix by heat welding, laser, ultrasonic wave, etc.

Moreover, as illustrated in FIG. 2, an arrowhead part 27 is formed at the top end of the each of the microneedle part first elements 15. The arrowhead part 27 has a shape of becoming thinner and sharper toward the top end side (the upper side of FIG. 2 (*c*)). Moreover, the arrowhead part 27 has a shape of protruding from the bonding section 25 of the first divisional element 9, and the height of protrusion of the arrowhead part 27 from the bonding section 25 of the first divisional element 9 (the size in the right and left directions of FIG. 2 (*c*), $H_2$) is substantially the same as the thickness of the second divisional element 11 (the size in the right and left directions of FIG. 2 (*c*), $T_1$).

Moreover, as illustrated in FIG. 2, an arrowhead part 29 is also formed at the top end (the bottom end of FIG. 2 (*a*)) of the each of the medicinal solution supply needle part first elements 17. The arrowhead part 29 also has a shape of becoming thinner and sharper toward the top end side (the lower side of FIG. 2 (*a*)). Moreover, the arrowhead part 29 also has a shape of protruding from the bonding section 25 of the first divisional element 9, and the height of protrusion of the arrowhead part 29 from the bonding section 25 of the first divisional element 9 (the size in the right and left directions of FIG. 2 (*a*), $H_3$) is substantially the same as the thickness of the second divisional element 11 (the size in the right and left directions of FIG. 2 (*a*), $T_1$).

Moreover, as illustrated in FIG. 2 (*b*), depressing projections 31, 31 are protrusively formed, respectively, at the both ends of the first divisional element main body 13 in the width direction (the right and left directions of FIG. 2 (*b*)).

Moreover, as illustrated in FIG. 1 and FIG. 2, the second divisional element 11 is a sheet-shaped member, composed of a second divisional element main body 37; a plurality of (in the first embodiment, six) microneedle part second elements 39 protrusively disposed on the upper side of the second divisional element main body 37 as seen in FIG. 1; and a plurality of (in the first embodiment, two) medicinal solution supply needle part second elements 40 protrusively disposed on the lower side of the second divisional element body 37 as seen in FIG. 1.

Moreover, as illustrated in FIG. 2 (*c*), the top edge part of the microneedle part second element 39 of the second divisional element 11 has been chamfered, so as to for a chamfered part 32. Because of molding workability and thickness of sheet material, etc., where the thickness of the second divisional element 11 (the size in the right and left directions of FIG. 1, $T_1$) becomes slightly higher than the height of protrusion of the arrowhead part 27 from the bonding section 25 of the first divisional element 9 (the size in the right and left directions of FIG. 2 (*a*), $H_2$), the chamfered part 32 is effective to reduce resistance during puncturing, and also to prevent separation of the second divisional element 11.

Note that, as long as the thickness of the second divisional element 11 (the size in the right and left directions of FIG. 1, $T_1$) is not higher than the height of protrusion of the arrowhead part 27 from the bonding section 25 of the first divisional element 9 (the size in the right and left directions of FIG. 2 (*a*), $H_2$), the chamfered part 32 is not necessarily required.

Moreover, likewise the case of the first divisional element 9, the second divisional element 11 may be made of, for example, versatile plastic such as polycarbonate or polyethylene, or biodegradable plastic such as polylactic acid or polyglycolic acid, and it is preferable to be made of biodegradable plastic from the viewpoint of biosafety.

Note that, it is also possible to manufacture the second divisional element 11 by using a material different from that of the first divisional element 9.

Moreover, although the second divisional element is also manufactured, for example, by injection molding, it is also possible to be manufactured by cutting a versatile film material, sheet material or tape material, etc. In this case, it is possible to cut the film material, etc., in advance in a shape of the first divisional element 9, so as to be bonded, thereafter, to the first divisional element 9. Further, it is also possible to bond the film material, etc., to the first divisional element 9, so as to be cut, thereafter, in an outer shape of the first divisional element 9.

Note that, where the second divisional element 11 is formed by injection molding, since the outer shape of the second divisional element 11 is also formed during molding, the cutting of the film material, etc., as described above is not required.

Moreover, although the width of the microneedle part second element 39 of the second divisional element ($W_4$) and the width of the microneedle part first element 15 of the first divisional element 9 ($W_5$) are set to be the same with each other, it is also possible to set the width of the microneedle part second element 39 of the second divisional element ($W_4$) to be smaller than the width of the microneedle part first element 15 of the first divisional element 9 ($W_5$). In this case, it is possible to compensate the unevenness of sizes during bonding. Moreover, during puncturing, this structure also effectively prevents unintended separation of the microneedle part second element 39.

Moreover, the microneedle 5 is composed, by the microneedle part second element 39 of the second divisional element 11, and by the microneedle part first element 15 of the first divisional element 9. Not only the upper surface of the second divisional element 11 (the surface on the left of FIG. 2 (*a*)) and the lower surface of the first divisional element 9 (the surface on the right of FIG. 2 (*a*)), but also, with regard to the microneedle 5 after being assembled, the upper surface (the surface on the left of FIG. 2 (*a*)) and the lower surface (the surface on the right of FIG. 2 (*a*)) thereof, are all in a flat shape.

The plurality of (in the first embodiment, six) microneedles 5 is disposed on a flat surface, and in the first embodiment, for example as illustrated in FIG. 1 (*a*), they are disposed uniformly in an array in the width direction (in the right and left directions of FIG. 1). Moreover, each of the microneedles 5 has the equal length (the size in the upward and downward directions of FIG. 1 (*a*), $L_1$), and as seen in the upward and downward directions of FIG. 1, each end position thereof on the basement side (the end position on the lower side of FIG. 1 (*a*)) is aligned.

Note that, when necessary, it is also possible to vary the length of each microneedle 5 (the size in the upward and downward directions of FIG. 1 (*a*), $L_1$) to be different from each other. This can be readily accepted with the injection molding by using the upper mold and the lower mold as described above.

Note that, the number of microneedles 5 is determined appropriately, depending on the position to be injected, the area of that position, the volume of medicinal solution, etc., and preferably, may be set to 1 to 50/cm, and more preferably, 5 to 20/cm.

Moreover, the width ($W_2$, the same as the width of the microneedle part second element 39 ($W_4$)) and the height ($H_4$) of the microneedle 5 is determined appropriately by considering the strength of the microneedle 5 and the relief of pain during puncturing, and preferably, may be set to 0.1 mm to 0.4 mm, and more preferably, 0.2 mm to 0.3 mm.

Moreover, the length of the microneedle 5 ($L_1$) is determined appropriately depending on the object of treatment (the applicable medicinal solution), and preferably, may be set around 0.3 mm to 3.0 mm, and for example, if the applicable medicinal solution is a vaccine, since the injection is performed from the epidermis to the upper layer of dermis, may be set around 0.5 mm to 1.5 mm.

Moreover, the interval between each of the microneedles 5 ($P_1$) is determined depending on the number, etc., of the microneedles 5, and preferably, may be set to 0.3 mm to 5.0 mm, and more preferably, 0.5 mm to 2.5 mm.

Moreover, the unit main body 3 is composed, by the second divisional element main body 37 of the second divisional element 11, and by the first divisional element main body 13 of the first divisional element 9.

Also with regard to the unit main body 3, likewise the case of the microneedle 5, the upper surface (the surface on the left of FIG. 2 (*a*)) and the lower surface (the surface on the right of FIG. 2 (*a*)) thereof, are both in a flat shape.

Moreover, the medicinal solution supply needle 7 is composed, by the medicinal solution supply needle part second element 40 of the second divisional element 11, and by the medicinal solution supply needle part first element 17 of the first divisional element 9.

Also with regard to the medicinal solution supply needle 7, likewise the case of the microneedle 5, the upper surface (the surface on the left of FIG. 2 (*a*)) and the lower surface (the surface on the right of FIG. 2 (*a*)) thereof, are both in a flat shape.

As already explained above, the number of the medicinal solution supply needles 7 is set to be less than the number of the microneedles 5, and is determined appropriately depending on the number of the microneedles 5 and the volume of supplied medicinal solution. Moreover, the plurality of medicinal solution supply needles 7 is disposed in balance with the plurality of microneedles 5, whereby the medicinal solution is delivered uniformly to the plurality of microneedles 5.

Moreover, the width ($W_3$) and the height ($H_5$) of the medicinal solution supply needle 7 is determined appropriately by considering the strength, the secured puncturing into a seal member (which will be described afterwards), the prevention of medicinal solution leakage, and the user friendliness, and preferably, may be set equivalent to 22 G (gauge) to 33 G (gauge) (0.2 mm to 0.7 mm), and more preferably, equivalent to 25 G (gauge) to 30 G (gauge) (0.3 mm to 0.5 mm).

Moreover, the second divisional element 11 blocks the communication path 23 completely. Moreover, the second divisional element 11 also blocks the microneedle side flow channels 19 except for the top end sides thereof (the upper side of FIG. 1 (b), and the second divisional element 11 also blocks the medicinal solution supply needle side flow channels 21 except for the top end sides thereof (the lower side of FIG. 1 (b)). Accordingly, a medicinal solution outlet 33 is provided on the top end side (the upper side of FIG. 1 (b)) of the microneedle side flow channel 19, and a medicinal solution inlet 35 is provided on the top end side (the lower side of FIG. 1 (b)) of the medicinal solution supply needle side flow channel 21.

Note that, the medicinal solution outlet 33 is provided as a downwardly-opening hole, so as to be oriented toward the skin during puncturing.

Next, the function of the first embodiment is explained.

According to the microneedle unit 1 of the first embodiment, the medicinal solution supply needles 7 puncture and are immersed into an unillustrated medicinal solution retaining part, and in this state, the microneedles 5 are used, for example, by puncturing thereof into the skin as an object of injection. Accordingly, the medicinal solution filled and retained in the retaining part is injected subcutaneously or intracutaneously.

To explain more in detail, the medicinal solution in the medicinal solution retaining part is supplied from the medicinal solution inlets 35 of the medicinal solution supply needles 7, and via the medicinal solution supply needle side flow channels 21, the communication path 23 and the microneedle side flow channels 19, the medicinal solution is discharged subcutaneously or intracutaneously from the medicinal solution outlets 33 of the microneedles 5.

Next, the effect of the first embodiment is explained.

First, the microneedle unit 1 according to the first embodiment is provided with the microneedles 5 and the medicinal solution supply needles 7, and with regard to the medicinal solution supply side, with the simple puncturing and immersing of the medicinal solution supply needles 7 into the medicinal solution retaining part, it is possible to accomplish the structure for supplying a desired medicinal solution, whereby the structure of the medicinal solution supply side can be simplified with the easy connectivity.

Moreover, since the plural number of microneedles 5 is provided, it is possible to perform the injection efficiently in a broad area.

Moreover, as illustrated in FIG. 1 and FIG. 2, since the microneedles 5 are disposed on a flat surface, namely in an array in the width direction (in the right and left directions of FIG. 2), the puncturing into the skin can be performed easily.

Moreover, via the communication path 23, the all microneedle side flow channels 19 and the all medicinal solution supply needle side flow channels 21 are communicating with each other, with maintaining the balance in the right and left directions of FIG. 2 (b). Therefore, the medicinal solution can be delivered efficiently and uniformly into each of the microneedles 5.

Moreover, where the length of the medicinal solution supply needle side flow channel 21 and the length of each of the microneedle side flow channels 19 are set to be equal to each other, the uniformity thereof will become more preferable.

Moreover, the width ($W_1$) and the depth ($H_1$) of the medicinal solution supply needle side flow channels 21, the communication path 23 and the microneedle side flow channels 19 are set to become smaller gradually, in the order the medicinal solution supply needle side flow channels 21, the communication path 23 and the microneedle side flow channels 19. Therefore, the flow channel resistance of the medicinal solution in the flow channels becomes small, and the injection from the microneedles 5 can be performed smoothly.

Moreover, since the microneedle unit 1 is composed, for example, by bonding of the first divisional element 9 with the second divisional element 11, it is possible to increase the freedom of design of the interior and inner channels thereof.

Moreover, the arrowhead part 27 is formed in the microneedle 5, and the height of protrusion of the arrowhead part 27 from the bonding section 25 of the first divisional element 9 (the size in the right and left directions of FIG. 2 (c), $H_2$) is substantially the same as the thickness of the second divisional element 11 (the size in the right and left directions of FIG. 2 (c), $T_1$). Therefore, during puncturing by the microneedles 5, it is possible to prevent separation of the second divisional element 11 due to interference with the skin, etc., as the object of puncturing.

Moreover, the tips of the microneedle 5 and the medicinal solution supply needle 7 are formed, not by bonding of the first divisional element 9 with the second divisional element 11, but by the first divisional element 9 only. Therefore, the tips of the microneedle 5 and the medicinal solution supply needle 7 can be strengthened.

Moreover, as illustrated in FIG. 2 (c), the medicinal solution outlet 33 is provided inwardly toward the right side from the arrowhead part 27 and the second divisional element 11 as seen in the right and left directions of FIG. 2 (c). Therefore, it is possible to prevent clogging of the medicinal solution outlet 33 by the skin tissue during puncturing.

Moreover, since the lower surface (the surface on the left of FIG. 2 (c)) and the upper surface (the surface on the right of FIG. 2 (c)) of the microneedle 5 are both in the flat shape, it is possible to reduce the resistance during puncturing.

Moreover, the thickness of the second divisional element 11 (the size in the right and left directions of FIG. 2 (c), T1), is substantially the same as the height of protrusion of the arrowhead part 29 from the bonding section 25 of the first divisional element 9 (the size in the right and left directions of FIG. 2 (a), H3). Therefore, during puncturing, it is possible to prevent the second divisional element 11 from being separated from the first divisional element 9 due to be caught by an unillustrated puncturing site of the medicinal solution retaining part.

Moreover, since the second divisional element 11 is a sheet-shaped member, the handling thereof during manufacturing, such as working and bonding of the first divisional element 9 with the second divisional element 11, can be performed easily.

Moreover, in the first embodiment, since the second divisional element 11 is also manufactured by injection molding, the cutting thereof, which is required when using a film material, is not required.

Note that, where the second divisional element 11 is manufactured by cutting a versatile film material, sheet material, tape material, etc., there is a wide scope of selection of the thickness, etc., of the material, and with the roll bonding, the bonding can be performed uniformly, and further, the high productivity can be accomplished.

Moreover, where the size of the second divisional element 11 is set to be smaller than the external shape of the first divisional element 9, the strict preciseness is not required for the purpose of bonding to the first divisional element 9, and therefore the manufacturing can be facilitated. Moreover, it is also possible to prevent separation of the second divisional element 11 during puncturing.

Next, a second embodiment of the present invention will be explained with reference to FIG. 3. As illustrated in FIG. 3, although a microneedle unit 41 according to the second embodiment has substantially the same structure as that of the microneedle unit 1 of the first embodiment, in the case of the microneedle unit 41, the both sides of the arrowhead part 29 of the medicinal solution supply needle 7 is protruding in the right and left directions of FIG. 3 (b), to form barb parts 43, 43, respectively.

Note that, the other structure is substantially the same as that of the first embodiment, and therefore, the same reference numerals are allotted to the same elements as those of the first embodiment in the drawings, and the explanation thereof is omitted.

Moreover, also in FIG. 3 (b) the bonding section 25 for bonding the first divisional element 9 with the second divisional element 11 is expressed by shading, defined by imaginary lines in FIG. 3 (b).

The microneedle unit 41 according to the second embodiment can accomplish substantially the same function and effect as those of microneedle unit 1 according to the first embodiment.

Further, with regard to the microneedle unit 41 of the second embodiment, the barb parts 43, 43 are protrusively formed in the arrowhead parts 29 of the medicinal solution supply needles 7, respectively. Therefore, for example, when the medicinal solution supply needles 7 are punctured into the medicinal solution retaining part, it is possible to prevent the medicinal solution supply needles 7 from unintended drop-off from the medicinal solution retaining part.

Accordingly, with the barb parts 43, 43, the medicinal solution supply needles 7 are not easily pulled out from the medicinal solution retaining part. Therefore, after puncturing of the microneedles 5 into the skin, when pulling out thereof, with the resistance caused between the barb parts 43, 43 of the medicinal solution supply needles 7 and the medicinal solution retaining part, it is possible to pull out the microneedles 5 from the skin securely.

Note that, in the second embodiment, likewise the case of the first embodiment, with regard to the manufacturing by injection molding, the directions of mold removal are set to be orthogonal to the axis directions of the microneedles 5 and the medicinal solution supply needles 7 (for example, in the directions perpendicular to the drawing sheet surface of FIG. 3 (b)). Therefore, there is no problem even in the structure in which the barb parts 43, 43 are protrusively formed.

Next, a third embodiment of the present invention will be explained with reference to FIG. 4 to FIG. 7.

As illustrated in FIG. 4, an injection device 51 according to the third embodiment is composed of; a medicinal solution retaining part 53 for retaining a medicinal solution 63; a depressing mechanism 55, which is disposed in the lower side of the medicinal solution retaining part 53 in FIG. 4 and which extrudes the medicinal solution 63 from the medicinal solution retaining part 53; and the microneedle unit 1 according to the first embodiment.

Figure 5B:
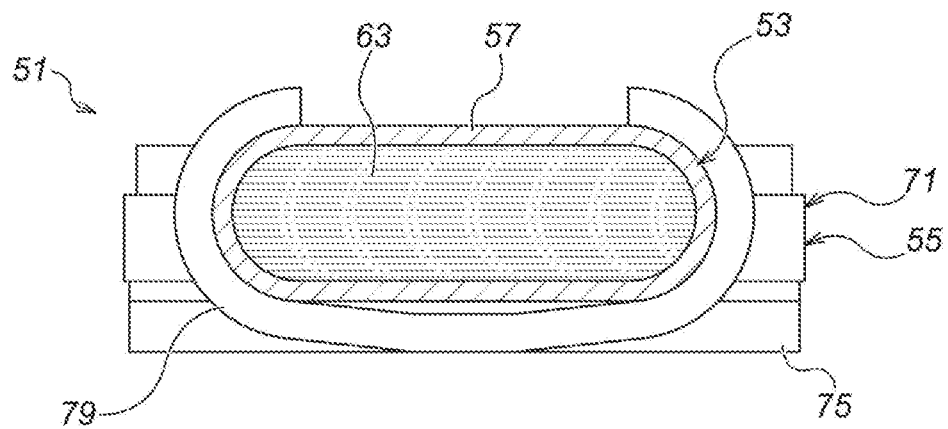

The medicinal solution retaining part 53 is provided, first, with a medicinal solution retaining part main body 57. The medicinal solution retaining part main body 57 is manufactured, for example, by injection molding of a resin material, and as illustrated in FIG. 5, is composed as a flattened hollow cylindrical body along the alignment direction of the microneedles 5 of the microneedle unit 1 (in the right and left directions of FIG. 5). Accordingly, the overall shape of the injection device 51 is also in the flattened shape.

As illustrated in FIG. 4, a medicinal solution supply side seal member holding part 58 is protrusively formed on the top end side of the medicinal solution retaining part main body 57 (the upper side of FIG. 4), and a medicinal solution supply side seal member 59 is inserted with pressure into the medicinal solution supply side seal member holding part 58. The medicinal solution supply side seal member 59 is formed by an elastic member, which is made of, for example, rubber such as silicone rubber, butyl rubber, isoprene rubber, polyurethane rubber, etc., or elastomer such as thermoplastic elastomer, etc. Moreover, in a using state, as illustrated in FIG. 4 and FIG. 6 (b), the medicinal solution supply side seal member 59 is punctured and penetrated by the medicinal solution supply needles 7, 7 of the microneedle unit 1.

Moreover, as illustrated in FIG. 4 (b), a depressing side seal member 61 is provided in the inside of the medicinal solution retaining part main body 57. The depressing side seal member 61 is also formed by an elastic member, likewise the case of the medicinal solution supply side seal member 59. Moreover, the medicinal solution 63 as described above is filled and retained, in the space between the depressing side seal member 61 in the medicinal solution retaining part main body 57 and the medicinal solution supply side seal member 59.

Figure 6A:
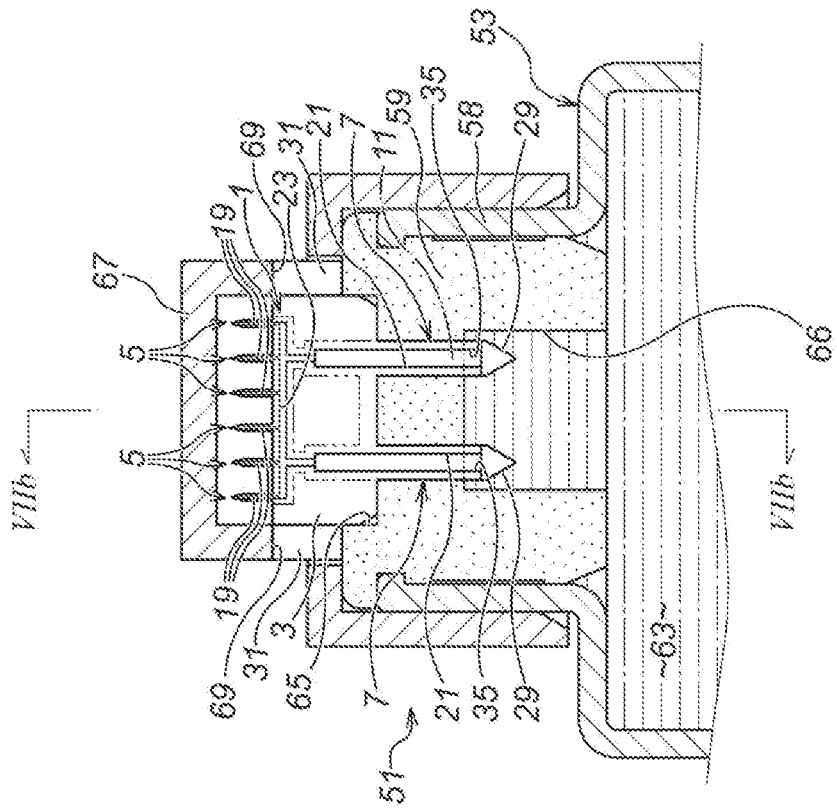
FIG. 6 Drawings showing the third embodiment of the present invention, namely.
Figure 6B:
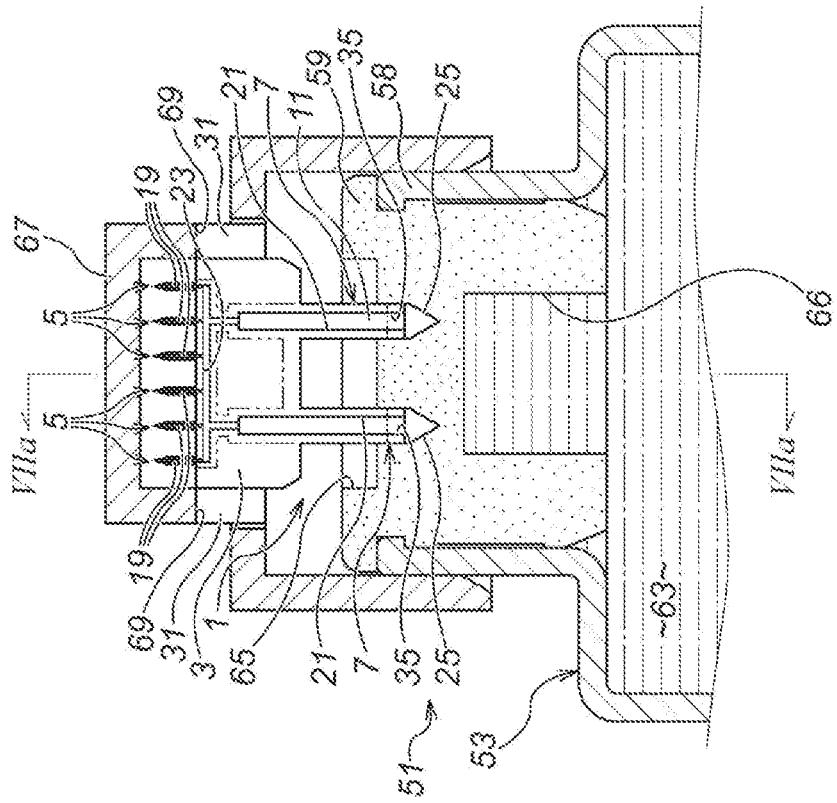

Moreover, as illustrated in FIG. 4 and FIG. 6, the microneedle unit 1 is provided on the upper side of the medicinal solution supply side seal member 59. In a non-use state, as illustrated in FIG. 6 (a), although the medicinal solution supply needles 7, 7 of the microneedle unit 1 are puncturing into the medicinal solution supply side seal member 59, they do not penetrate therethrough to reach the side of the medicinal solution 63 (the lower side of FIG. 6). On the other hand, in the using state, as illustrated in FIG. 4 and FIG. 6 (b), the medicinal solution supply needles 7, 7 of the microneedle unit 1 penetrate through the medicinal solution supply side seal member 59, and the medicinal solution inlets 35 are immersed in the medicinal solution 63. Thus, the medicinal solution 63 is supplied to the side of the microneedle unit 1 via the medicinal solution supply needles 7, 7.

Moreover, as illustrated in FIG. 6, an upper side recess 65, which is opening upwardly in FIG. 6, is formed in the medicinal solution supply side seal member 59. Thus, when the medicinal solution side seal member 59 is penetrated by the medicinal solution supply needles 7, 7 of the microneedle unit 1, the lower side of the unit main body 3 of the microneedle unit 1, as seen in FIG. 6, is accommodated in the upper side recess 65.

Moreover, a lower side recess 66, which is opening downwardly in FIG. 6, is formed in the medicinal solution supply side seal member 59. Thus, when the medicinal solution supply side seal member 59 is penetrated by the medicinal solution supply needles 7, 7 of the microneedle unit 1, the side of each of the medicinal solution inlets 35 of the medicinal solution supply needles 7, 7 (the lower side of FIG. 6) protrudes into the lower side recess 66. Accordingly, the length of the each of the medicinal solution supply needles 7, 7 (the size in the upward and downward directions of FIG. 6) can be shortened, and at the same time, the insertion length of the medicinal solution supply side seal member 59 (the length in the upward and downward directions of FIG. 6) into the medicinal solution supply side seal member holding part 58 can be lengthened sufficiently to secure the sealing tightness.

Moreover, as illustrated in FIG. 7, the microneedle unit 1 is provided on the medicinal solution supply side seal member 59, in a state that the second divisional element 11 is positioned on the left side of FIG. 7. Moreover, the microneedle unit 1 is disposed, so as to offset from the center toward the left side of the medicinal solution retaining part main body 57, as well as of the injection device 51, as seen in the right and left directions of FIG. 7. Moreover, as already explained in the first embodiment, with regard to the microneedle unit 1, the microneedles 5 are disposed so as to offset toward the side of the second divisional element 11. Accordingly, the microneedles 5 are disposed to as to largely offset toward the left side of FIG. 7, and consequently, it is possible to perform an inclined puncturing easily, in a state that the second divisional element 11 is positioned on the side of the object of puncturing (for example, the skin).

Note that, when the microneedles 5 are inclined, for example, even where the skin is deformed, it is possible to puncture the microneedles 5 securely into the skin.

Moreover, as illustrated in FIG. 6, a cap 67 covers the top end side of the medicinal solution retaining part 53 (the upper side of FIG. 6). The cap 67 is manufactured, for example, by injection molding of a resin material, and protects the microneedles 5 of the microneedle unit 1, and further, in the using state, is depressed toward the side of the medicinal solution supply side seal member 59 (toward the lower side of FIG. 6) together with the microneedle unit 1. Thus, the medicinal solution supply needles 7, 7 penetrate through the medicinal solution supply side seal member 59, whereby the medicinal solution inlets 35 are immersed into the medicinal solution 63 in the medicinal solution retaining part 53.

Depressing engagement grooves 69, 69 are formed, respectively, on the both sides of the cap 67 in the width direction thereof (the right and left directions of FIG. 6 (*a*)), and the depressing projections 31, 31 of the microneedle unit 1 are engaged, respectively, with the depressing engagement grooves 69, 69. Thus, when the cap 67 is depressed toward the side of the medicinal solution supply side seal member 59 (downwardly in FIG. 6), via the depressing projections 31, 31, the microneedle unit 1 is depressed toward the side of the medicinal solution supply side seal member 59 (downwardly in FIG. 6).

Moreover, with regard to the depressing mechanism 55, first, there is a depressing mechanism main body 71 provided on the lower side of the medicinal solution retaining part main body 57 as seen in FIG. 4. The depressing mechanism main body 71 is substantially in a U-shaped form with elasticity, and manufactured, for example, by injection molding of a resin material.

As illustrated in FIG. 4 (*b*), engagement projections 72, 72 are formed, respectively, on the both ends of the depressing mechanism main body 71 (on the upper side of FIG. 4 (*b*)), and the engagement projections 72, 72 are engaged, respectively, with upper ends 73*a*, 73*a* of engagement slits 73, 73 formed on the lower side of the medicinal solution retaining part main body 57 as seen in FIG. 4 (*b*).

Moreover, as illustrated in FIG. 4 (*a*), an inverted V-shaped arm 75 is connected to the upper side of the depressing mechanism main body 71 as seen in FIG. 4 (*a*). The inverted V-shaped arm 75 is also manufactured, for example, by injection molding of a resin material. The both ends of the inverted V-shaped arm 75 and the both ends of the depressing mechanism main body 71 are rotatably connected, respectively, via pins 76, 76, respectively. Moreover, an operating member 79 in a circular shape is provided on the upper side of the inverted V-shaped arm 75. The operating member 79 is also manufactured, for example, by injection molding of a resin material.

Thus, as illustrated in FIG. 4 (*a*), when the operating member 79 is moved along the medicinal solution retaining part main body 57 in the downward direction of FIG. 4 (*a*), a center part 77 of the inverted V-shaped arm 75 is depressed in the downward direction of FIG. 4 (*a*), and the both ends of the inverted V-shaped arm 75 as well as those of the depressing mechanism main body 71 are deformed to expand outwardly.

Moreover, as illustrated in FIG. 4 (*b*), a piston 81 is provided in the inside of the medicinal solution retaining part 53, on the lower side of the depressing side seal member 61. The piston 81 is also manufactured, for example, by injection molding of a resin material. A spring engagement part 83 is formed in the piston 81, and another spring engagement part 85 is also formed in the depressing mechanism main body 71 on the side opposing to the piston 81. A coil spring 87 is provided with the tension between the spring engagement parts 83 and 85. With the elastic force of the coil spring 87, the piston 81 is always depressed upwardly in FIG. 4 (*b*).

Moreover, engagement parts 89, 89, formed on the both ends of the piston 81, are engaged, respectively, with the engagement projections 72, 72 of the depressing mechanism main body 71, or with the upper ends 73*a*, 73*a* of the engagement slits 73, 73 of the medicinal solution retaining part main body 57. Accordingly, the movement of the piston 81 in the upward direction of FIG. 4 (*b*) and FIG. 4 (*c*) is prohibited, whereby a locking mechanism of the piston 81 is constituted.

Note that, when the locking mechanism of the piston 81 is released, with the elastic force of the coil spring 87, the medicinal solution 63 is discharged gradually from the medicinal solution outlets 33 of the microneedles 5.

Note that, in FIG. 4 and FIG. 6, for the sake of explanation convenience, the external shape of the second divisional element 11 of the microneedle unit 1 is expressed by imaginary lines.

Next, the function of the third embodiment is explained.

The microneedle unit 1 and the injection device 51 according to the third embodiment are used in the following manner:

In the non-use state, the microneedle unit 1 is in a state as shown in FIG. 6 (*a*) and FIG. 7 (*a*). The medicinal solution supply needles 7, 7 do not penetrate through the medicinal solution supply side seal member 59, and the medicinal solution 63 is filled and retained in the medicinal solution retaining part main body 57.

In the using state, with the depressing of the cap 67 toward the side of the medicinal solution retaining part 53 (downwardly in FIG. 6), the microneedle unit 1 is biased, and as illustrated in FIG. 6 (*b*) and FIG. 7 (*b*), the medicinal solution supply needles 7, 7 penetrate through the medicinal solution supply side seal member 59. Thereafter, the cap 67 is removed.

Next, the air extraction of the microneedle unit 1 is performed, so as to discharge the air to the outside, and to fill the medicinal solution 63 therein.

Note that, before the air extraction, the injection device 51 is in a state as shown in FIG. 4 (*b*). In this state, the engagement projections 72, 72 of the depressing mechanism main body 71 are engaged, respectively, with the upper ends 73a, 73a of the engagement slits 73, 73 of the medicinal solution retaining part main body 57, and further, the engagement parts 89, 89 of the piston 81 are engaged, respectively, with the lower sides of the engagement projections 72, 72.

In this state, when the operating member 79 is depressed in the downward direction of FIG. 4, the both ends of the depressing mechanism main body 71 are deformed to expand outwardly. At that time, the engagement of the engagement projections 72, 72 of the depressing mechanism main body 71, with the engagement slits 73, 73 of the medicinal solution retaining part main body 57, and also with the engagement parts 89, 89 of the piston 81, are released, respectively, and with the elastic force of the coil spring 87, the piston 81 is depressed upwardly toward the side of the microneedle unit 1 (in the upward direction of FIG. 4). Accordingly, the air in the microneedle unit 1 is discharged from the medicinal solution outlets 33 of the microneedles 5, 5, and at the same time, the inside of the microneedle unit 1 is filled with the medicinal solution 63.

And thus, the piston 81 is depressed upwardly as much as the height of the engagement projections 72, 72 of the depressing mechanism main body 71 (the size in the upward and downward directions of FIG. 4), and the engagement parts 89, 89 are engaged, respectively, with the upper ends 73a, 73a of the engagement slits 73, 73 of the medicinal solution retaining part main body 57, whereby the movement toward the microneedle 1 (in the upward direction of FIG. 4) is prohibited. At that time, the injection device 51 is in a state as shown in FIG. 4 (c).

Next, the microneedles 5 of the microneedle unit 1 are punctured into the object of puncturing (for example, the skin).

Next, the depressing mechanism main body 71 is depressed from the both sides in the width direction (in the right and left directions of FIG. 4), whereby the engagement of the engagement parts 89, 89 of the piston 81 with the engagement slits 73, 73 of the medicinal solution retaining part main body 57 is released. At that time, as illustrated in FIG. 4 (d), with the elastic force of the coil spring 87, the piston 81 is further depressed upwardly toward the side of the microneedle unit 1 (in the upward direction of FIG. 4). Accordingly, the medicinal solution 63 in the medicinal solution retaining part main body 57 is gradually injected, via the microneedles 5, into the object of puncturing.

Next, the inclined puncturing is explained. In the case of the inclined puncturing, the whole body of the injection device 51 is largely inclined toward the side of the skin, so that the medicinal solution outlet 33 formed as the downwardly-opening hole in the microneedle 5 is disposed to face in the proximity of the skin, and in this state, the microneedles 5 of the microneedle unit 1 are punctured into the object of puncturing (for example, the skin).

Thereafter, the injection is performed in accordance with the same function as described above.

Next, the effect of the third embodiment is explained.

First, also in the third embodiment, the same effect as that of the microneedle unit 1 of the first embodiment can be accomplished.

Moreover, as illustrated in FIG. 5, the medicinal solution retaining part main body 57, as well as the injection device 51, are in the flattened shape along the alignment direction of the microneedles 5 of the microneedle unit 1 (the right and left directions of FIG. 5), and there is no structural element in the direction orthogonal to the alignment direction of the microneedles 5 (the right and left directions of FIG. 5). Therefore, it is possible to perform the inclined puncturing easily, in the state that the whole body of the injection device 51 is largely inclined toward the side of the skin.

Moreover, with regard to the microneedle unit 1, the microneedles 5 are provided so as to offset toward the second divisional element 11, and with regard to the injection device 51, the microneedle unit 1 in itself is disposed so as to offset toward the second divisional element 11. Besides, with regard to the microneedle 5, the medicinal solution outlet 33 is provided as the downwardly-opening hole on the side of the second divisional element 11. With the synergetic function of these structures, the inclined injection can be performed more easily, and accordingly, it is also possible to perform the inclined puncturing in a state that the medicinal solution outlets 33 are disposed in the proximity of the skin.

Moreover, the injection can be performed in the inclined state of the microneedles 5. Therefore, for example, where the skin is deformed during puncturing, it is possible to puncture the microneedles 5 into the skin securely.

Moreover, since the medicinal solution outlet 33 is oriented to the side of the skin, it is possible to perform the injection securely by preventing leakage of the medicinal solution 63.

Moreover, when the microneedle unit 1 is installed in the injection device 51, it is sufficient to simply puncture the medicinal solution supply needles 7, 7 into the medicinal solution supply side seal member 59, whereby the injection device 51 can be completed easily.

Moreover, when the medicinal solution supply side seal member 59 is penetrated through the medicinal solution supply needles 7, 7, a certain degree of depressing force is required, and normally, such a depressing force is not caused. Therefore, there is no risk that the medicinal solution supply side seal member 59 would be unintentionally penetrated by the medicinal solution supply needles 7, 7, and it is possible to prevent unintended leakage of the medicinal solution 63.

Moreover, with the simple penetration of the medicinal solution supply needles 7, 7 through the medicinal solution supply side seal member 59, the ready-to-use state can be obtained, and the operation thereof is easy.

Moreover, since the cap 67 is provided, the microneedles 5 of the microneedle unit 1 can be protected, and further, it is also possible to prevent unintended puncturing of the microneedles 5.

Moreover, with the depressing of the cap 67 toward the side of the medicinal solution retaining part 53 (in the downward direction of FIG. 6), the microneedle unit 1 is biased, and as illustrated in FIG. 6 (b) and FIG. 7 (b), the medicinal solution supply side seal member 59 can be penetrated by the medicinal solution supply needles 7, 7, without touching the microneedles 5 during depressing.

Moreover, with the simple and slight movement of the piston 81 in the upward direction of FIG. 4 by depressing of the operating member 79 in the downward direction of FIG. 4, it is possible to perform the air extraction of the microneedle unit 1.

Moreover, after the air extraction, the engagement parts 89, 89 of the piston 81 are engaged, respectively, with the upper ends 73a, 73a of the engagement slits 73, 73 of the medicinal solution retaining part main body 57. Therefore, it is possible to prevent unintended discharge of the medicinal solution 63 before puncturing of the microneedles 5.

Moreover, with the simple depressing of only the both sides of the depressing mechanism main body 71 in the width direction (the right and left directions of FIG. 4), the engagement of the engagement parts 89, 89 of the piston 81, with the upper ends 73a, 73a of the engagement slits 73, 73 of the medicinal solution retaining part main body 57, can be released. Therefore, with the simple operation, it is possible to start injection by the injection device 51.

Moreover, the piston 81 is depressed upwardly toward the side of the microneedle unit 1 (in the upward direction of FIG. 4) by the coil spring 87. Therefore, with the appropriate setting of the elastic force of the coil spring 87, it is possible to adjust the discharging speed of the medicinal solution 63 from the medicinal solution outlets 33 of the microneedles 5.

Moreover, since the medicinal solution retaining part main body 57, the inverted V-shaped arm 75, the operating member 79 and the piston 81 are made by molding of a resin material, the manufacturing thereof is easy.

Next, a fourth embodiment of the present invention will be explained with reference to FIG. 8 to FIG. 10.

A microneedle unit 101 according to the fourth embodiment is substantially in the same structure as that of the microneedle unit 1 of the first embodiment. However, the communication path is partitioned at the center in the width direction thereof as seen in FIG. 8 (b), to be compartmented as a communication path 103 on the left of FIG. 8 (b) and a communication path 105 on the right of FIG. 8 (b).

Note that, FIG. 8 (b) is a plan view showing the first divisional element 9 only, by removing the second divisional element 11 from the microneedle unit 101. Moreover, in FIG. 8 (b), the bonding section 25 for bonding the first divisional element 9 with the second divisional element 11 is expressed by shading, defined by imaginary lines.

Moreover, the medicinal solution supply needle side flow channel 21 on the left side of FIG. 8 (b), the communication path 103, and three of the microneedle side flow channels 19, 19, 19 on the left side of FIG. 8 (b) are communicating with each other, and further, the medicinal solution supply needle side flow channel 21 on the right side of FIG. 8 (b), the communication path 105, and three of the microneedle side flow channels 19, 19, 19 on the right side of FIG. 8 (b) are communicating with each other.

Accordingly, a medicinal solution 117, supplied from the medicinal solution inlet 35 of the medicinal solution supply needle 7 on the left side of FIG. 8 (b), is discharged from the medicinal solutions outlets 33, 33, 33 of three of the microneedles 5, 5, 5 on the left side of FIG. 8 (b), and further, a medicinal solution 119, supplied from the medicinal solution inlet 35 of the medicinal solution supply needle 7 on the right side of FIG. 8 (b), is discharged from the medicinal solutions outlets 33, 33, 33 of three of the microneedles 5, 5, 5 on the right side of FIG. 8 (b).

Note that, with regard to the microneedle unit 101, the same reference numerals are allotted to the same elements as those of the microneedle unit 1 of the first embodiment, and the explanation thereof is omitted.

Figure 9A:
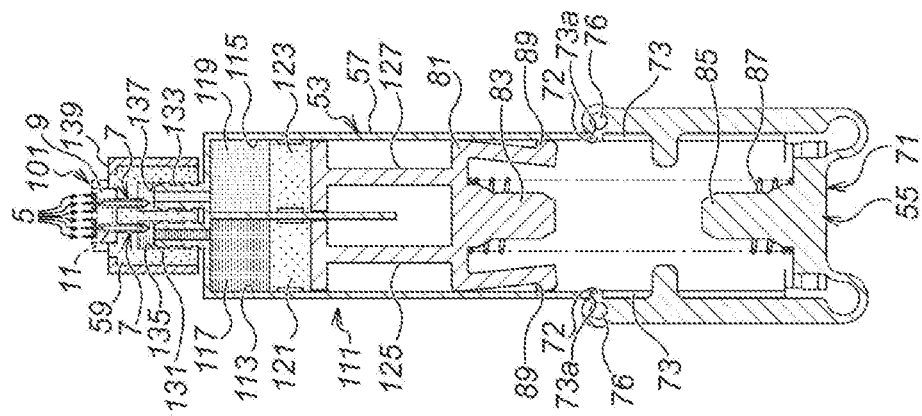
FIG. 9 Drawings showing the fourth embodiment of the present invention, namely.
Figure 9B:
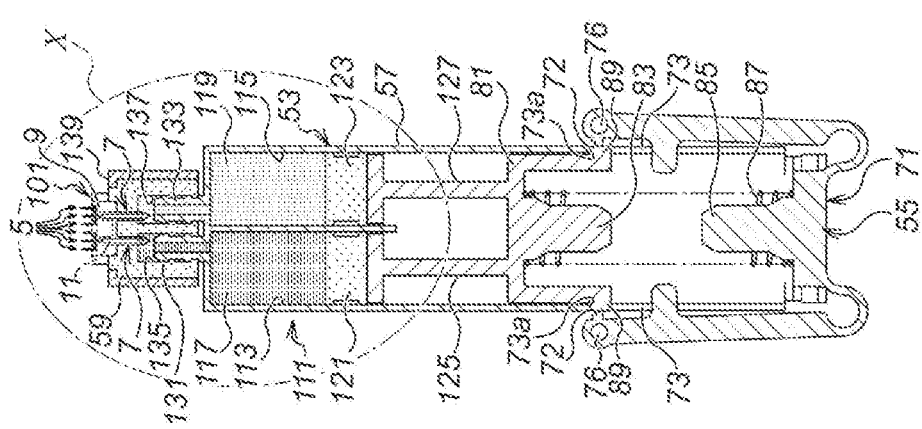
Figure 9C:
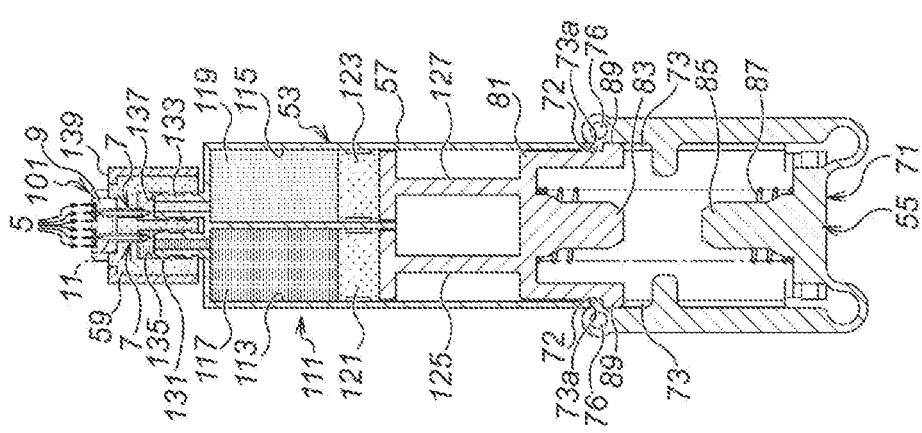

Moreover, as illustrated in FIG. 9, an injection device 111 according to the fourth embodiment has substantially the same structure as that of the injection device 51 of the third embodiment. However, corresponding to the structure of the microneedle unit 101, there are some different structural parts.

First, two chambers 113, 115 are provided in the inside of the medicinal solution retaining part main body 57. The chamber 113 is filled with and retains the medicinal solution 117, and the chamber 115 is filled with and retains the medicinal solution 119 in a different type.

Moreover, depressing side seal members 121, 123 are provided, respectively, in the chambers 113, 115. The depressing side seal members 121, 123 are depressed simultaneously by the piston 81. Depressing parts 125, 127 are protrusively formed in the piston 81 on the upper side of FIG. 9, whereby the depressing side seal member 121 is depressed via the depressing part 125, and the depressing side seal member 123 is depressed via the depressing part 127.

Moreover, connecting parts 131, 133 are formed on the top end side of the medicinal solution retaining part main body 57 (on the upper side of FIG. 9). Communication paths 131a, 133a are formed, respectively, in the connecting parts 131, 133. Moreover, with regard to the medicinal solution supply side seal member 59, connecting recesses 135, 137 are formed, respectively, to be opening toward the base end side (the lower side of FIG. 9), whereby the connecting part 131 is inserted into the connecting recess 135, and the connecting part 133 is inserted into the connecting recess 137. Moreover, the chamber 113 of the medicinal solution retaining part main body 57 is communicating with the inside of the connecting recess 135 of the medicinal solution supply side seal member 59 via the communication path 131a of the connecting part 131, and the chamber 115 of the medicinal solution retaining part main body 57 is communicating with the inside of the connecting recess 137 of the medicinal solution supply side seal member 59 via the communication path 133a of the connecting part 133.

Moreover, as illustrated in FIG. 9 (a), when the medicinal solution supply side seal member 59 is penetrated by the medicinal solution supply needles 7, 7 of the microneedle unit 101, the medicinal solution supply needle 7 on the left side of FIG. 9 (a) protrudes into the inside of the connecting recess 135 of the medicinal solution supply side seal member 59, and the medicinal solution supply needle 7 on the right side of FIG. 9 (a) protrudes into the inside of the connecting recess 137 of the medicinal solution supply side seal member 59.

Moreover, the outer periphery of the medicinal solution supply side seal member 59 is covered by a cover 139 substantially in a cylindrical shape. The microneedles 5 of the microneedle unit 101 is exposed on the top end side of the cover 139 (the upper side of FIG. 9).

Moreover, with regard to the injection device 111 according to the fourth embodiment, the same reference numerals are allotted to the same elements as those of the injection device 51 of the third embodiment, and the explanation thereof is omitted.

Figure 10:
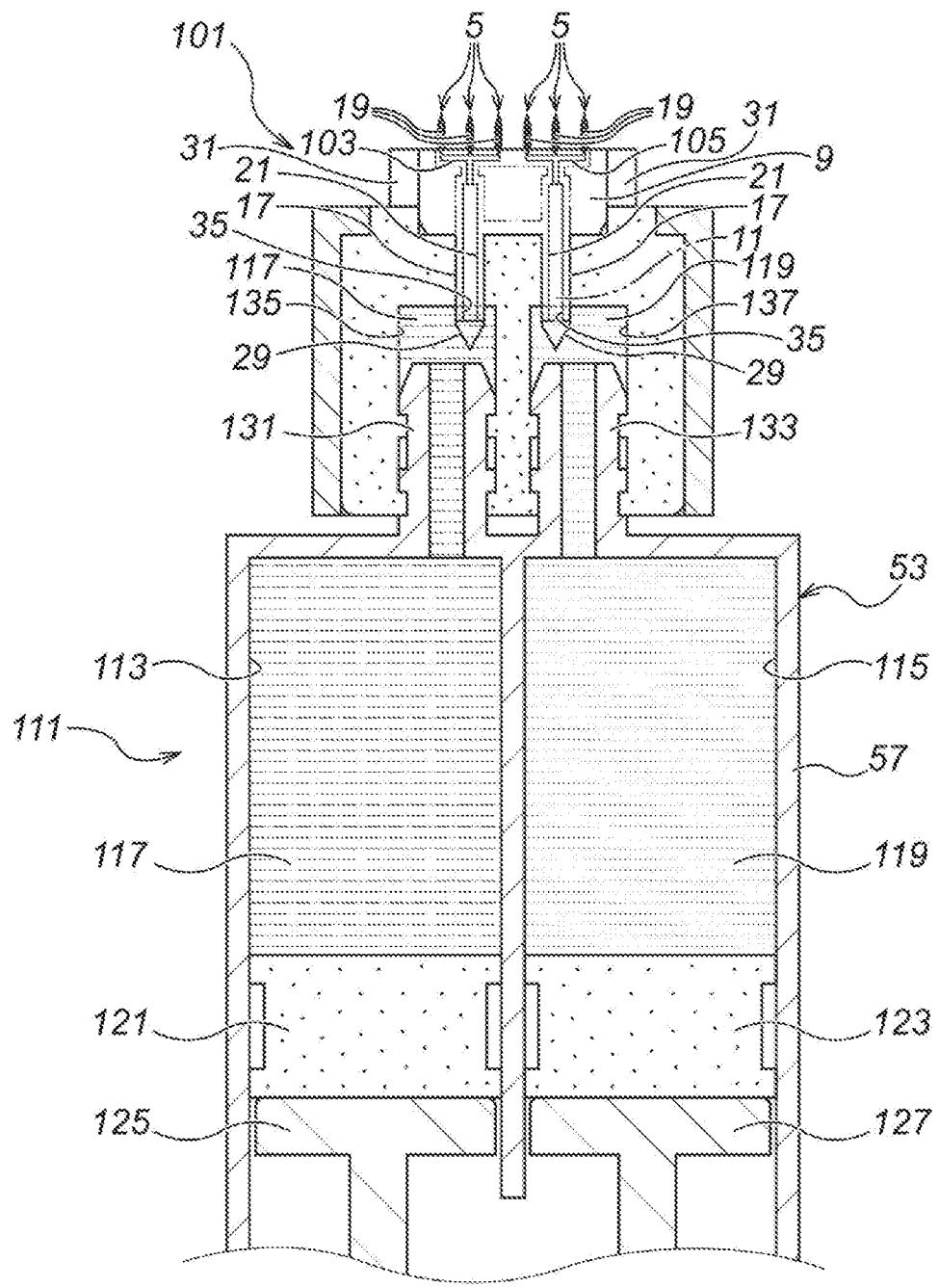
FIG. 10 A drawing showing the fourth embodiment of the present invention, namely, an expanded view of a section X of FIG. 9 (b).

Note that, in FIG. 9 and FIG. 10, for the sake of explanation convenience, the external shape of the second divisional element 11 of the microneedle unit 101 is expressed by imaginary lines.

Next, the function of the microneedle unit 101 and the injection device 111 according to the fourth embodiment is explained.

With reference to the microneedle unit 101 according to the fourth embodiment, as illustrated in FIG. 8, two communication paths 103, 105 are provided. The medicinal solution supply needle side flow channel 21 on the left side of FIG. 8, the communication path 103, and three of the microneedle side flow channels 19, 19, 19 on the left side of FIG. 8 are communicating with each other, and further, the medicinal solution supply needle side flow channel 21 on the right side of FIG. 8, the communication path 105, and three of the microneedle side flow channels 19, 19, 19 on the right side of FIG. 8 are communicating with each other. And thus, the medicinal solution 117 is supplied from the medicinal solution supply needle side flow channel 21 on the left side of FIG. 8, and the medicinal solution 119 in a different type is supplied from the medicinal solution supply needle side flow channel 21 on the right side of FIG. 8. Accordingly, the medicinal solution 117 is discharged from the medicinal solutions outlets 33, 33, 33 of three of the microneedles 5, 5, 5 on the left side of FIG. 8, and further, the medicinal solution 119 in a different type is discharged from the medicinal solutions outlets 33, 33, 33 of three of the microneedles 5, 5, 5 on the right side of FIG. 8.

Moreover, with regard to the injection device 111 according to the fourth embodiment, as illustrated in FIG. 9, the chambers 113, 115 are provided in the inside of the medicinal solution retaining part main body 57. The chamber 113 is filled with and retains the medicinal solution 117, and the chamber 115 is filled with and retains the medicinal solution 119. Thus, during injecting, the medicinal solution 117 in the chamber 113 and the medicinal solution 119 in the chamber 115 are extruded simultaneously by the piston 81, and as described above, the medicinal solution 117 is discharged from the medicinal solutions outlets 33, 33, 33 of three of the microneedles 5, 5, 5 on the left side of FIG. 9 (*c*), and further, the medicinal solution 119 is discharged from the medicinal solutions outlets 33, 33, 33 of three of the microneedles 5, 5, 5 on the right side of FIG. 9 (*c*).

Note that, the microneedle unit 101 according to the fourth embodiment may also be applied to the injection device 51 of the third embodiment. In this case, the same type of medicinal solutions are discharged from three microneedles 5, 5, 5 on the left side of FIG. 8 and also from three microneedles 5, 5, 5 on the right side of FIG. 8.

Next, the effect of the fourth embodiment is explained.

The chambers 113, 115 are provided in the inside of the medicinal solution retaining part main body 57, whereby the chamber 113 is filled with and retains the medicinal solution 117, and the chamber 115 is filled with and retains the medicinal solution 119. Therefore, it is possible to retain two types of the medicinal solutions, of which mixing is prohibited during storing.

Moreover, during injecting, the medicinal solution 117 is discharged from the medicinal solutions outlets 33, 33, 33 of three of the microneedles 5, 5, 5 on the left side of FIG. 9 (*c*), and further, the medicinal solution 119 is discharged from the medicinal solutions outlets 33, 33, 33 of three of the microneedles 5, 5, 5 on the right side of FIG. 9 (*c*). Therefore, it is possible to perform injection of the medicinal solutions 117, 119 independently and simultaneously, of which types are different from each other, and of which mixing is prohibited even in the case of injecting.

Moreover, it is possible to handle two types of the medicinal solutions 117, 119, of which mixing is prohibited, by a single injection device 111 easily. Therefore, the burden on the user is relieved.

Next, a fifth embodiment of the present invention will be explained with reference to FIG. 11 to FIG. 13.

With regard to a microneedle unit 151 according to the fifth embodiment, a mixing chamber 153 is provided between the communication path 23 and the medicinal solution supply needle side flow channels 21, 21. The mixing chamber 153 is a chamber of which cross-section is substantially in a circular shape, communicating with the medicinal solution supply needle side flow channels 21, 21, respectively, at the both sides on the right and left of FIG. 11 (*a*), and also communicating with the communication path 23 at the center of FIG. 11 (*a*).

Moreover, the diameter of the mixing chamber 153 ($d_1$) is set to be larger than the width of the medicinal solution supply needle side flow channel 21 ($W_1$).

Note that, the depth of the mixing chamber 153 is set to be equal to the depth of the medicinal solution supply needle side flow channel 21.

Moreover, in the mixing chamber 153, the medicinal solution 117 supplied from the medicinal solution supply needle side flow channel 21 on the left side of FIG. 11 (*a*), and the medicinal solution 119 supplied from the medicinal solution supply needle side flow channel 21 on the right side of FIG. 11 (*a*), are mixed together. And thus, a mixed medicinal solution 163 is supplied to the side of the communication path 23.

Figure 12A:
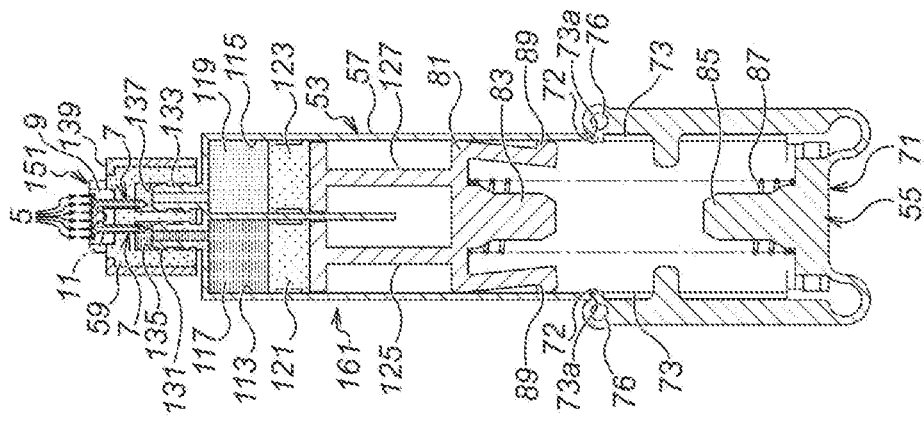
FIG. 12 Drawings showing the fifth embodiment of the present invention, namely.
Figure 12B:
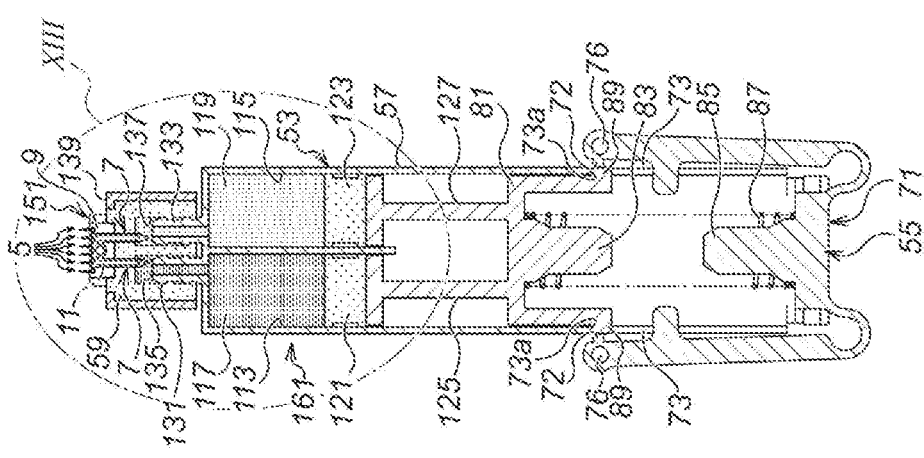
Figure 12C:
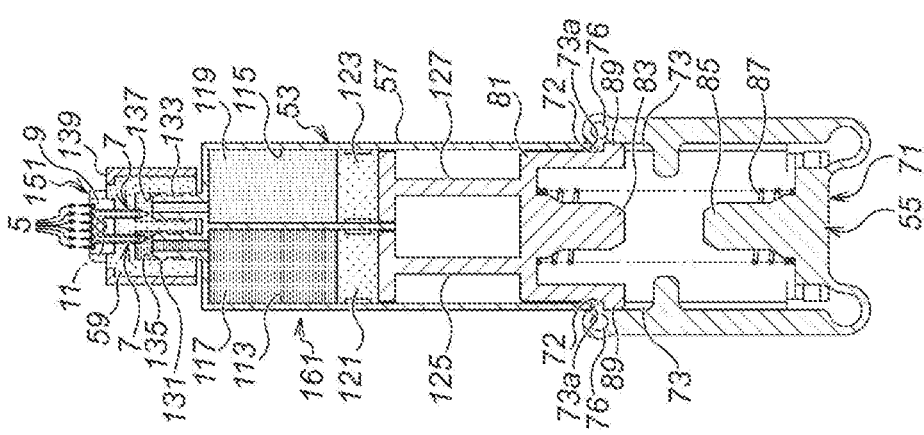

Moreover, as illustrated in FIG. 12, an injection device 161 according to the fifth embodiment has substantially the same structure as that of the injection device 111 of the fourth embodiment as described above, except for the structure that the microneedle unit 151 as described above is provided on the top end side thereof (on the upper side of FIG. 12).

Figure 13:
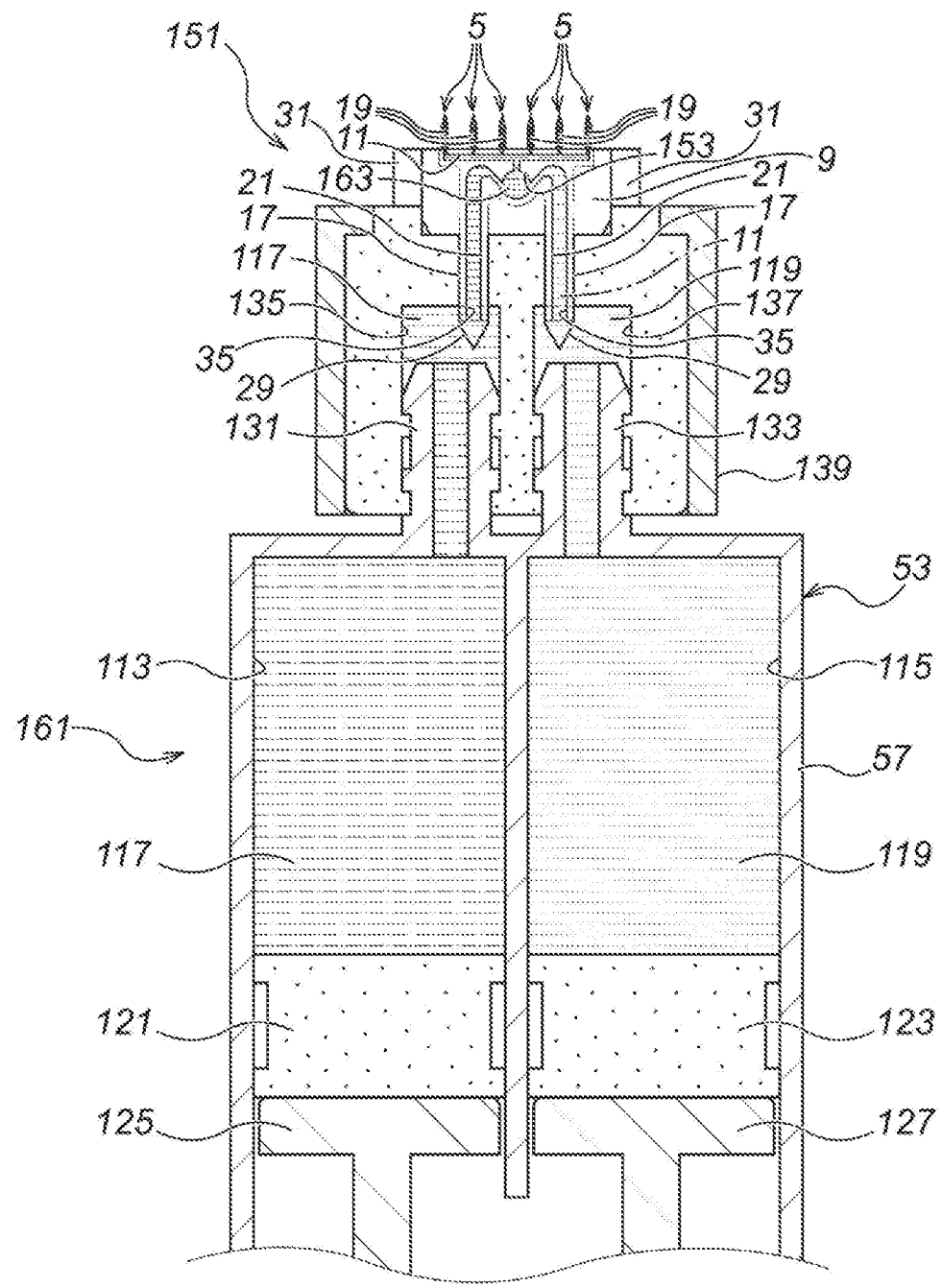
FIG. 13 A drawing showing the fifth embodiment of the present invention, namely, an expanded view of a section XIII of FIG. 12 (b).

Note that, in FIG. 11 and FIG. 13, for the sake of explanation convenience, the external shape of the second divisional element 11 of the microneedle unit 151 is expressed by imaginary lines.

Next, the function of the fifth embodiment is explained. The medicinal solution 117 supplied from the medicinal solution supply needle side flow channel 21 on the left side of FIG. 11 (*a*), and the medicinal solution 119 supplied from the medicinal solution supply needle side flow channel 21 on the right side of FIG. 11 (*a*), are mixed together in the mixing chamber 153, and the mixed medicinal solution 163 is supplied to the side of the communication path 23. And thus, the mixed medicinal solution 163 is discharged from the medicinal solution outlets 33 of the microneedles 5.

Thus, although the injection device 111 according to the fourth embodiment performs injection of two types of the medicinal solutions 117, 119 independently without mixing, the injection device 161 according to the fifth embodiment performs injection of the medicinal solution 163, which is the mixture of two types of the medicinal solutions 117, 119 as described above.

Next, the effect of the fifth embodiment is explained.

According to the fifth embodiment, it is also possible to accomplish substantially the same effect as that of the fourth embodiment, and further, in the case of the fifth embodiment, it is possible to perform injection of the medicinal solution 163, which is the mixture of two types of the medicinal solutions 117, 119.

Moreover, according to the fifth embodiment, it is possible to retain the medicinal solutions 117, 119 separately, and further, since the mixing chamber 153 is provided between the communication path 23 and the medicinal solution supply needle side flow channels 21, it is also possible to mix the medicinal solutions 117, 119 securely in the mixing chamber 153, so as to be supplied to each of the microneedles 5.

Moreover, as illustrated in FIG. 11 (*a*), the microneedles 5 are disposed uniformly along the width direction of the communication path 23, and a connecting part between the mixing chamber 153 and the communication path 23 is provided at the center of the communication path 23 in the width direction (the right and left directions of FIG. 11 (*a*)). Therefore, it is possible to supply the uniformly mixed medicinal solution 163 to each of the microneedles 5.

Moreover, the diameter of the mixing chamber 153 ($d_1$) is set to be larger than the width of the medicinal solution supply needle side flow channel 21 ($W_1$). Therefore, the volume of the mixing chamber 153 is larger, and to this extent, the mixing of two types of the medicinal solutions 117, 119 is facilitated.

Note that, the present invention is not limited to the first to fifth embodiments as described above.

First, according to the first to fifth embodiments, the height of protrusion of the arrowhead part 27 and the arrowhead part 29 from the bonding section 25 of the first divisional element 9 (the size in the right and left directions of FIG. 2 (c), $H_2$ and $H_3$) is set to be substantially the same as the thickness of the second divisional element 11 (the size in the right and left directions of FIG. 2 (c), $T_1$). However, it is also possible that the height of protrusion of the arrowhead part 27 and the arrowhead part 29 from the bonding section 25 of the first divisional element 9 (the size in the right and left directions of FIG. 2 (c), $H_2$ and $H_3$) is set to be larger than the thickness of the second divisional element 11 (the size in the right and left directions of FIG. 2 (c), $T_1$). Accordingly, during puncturing, it is possible to improve the separation prevention effect of the second divisional element 11.

Moreover, in the first to fifth embodiments, the medicinal solution outlet 33, provided at the top end of the microneedle 5 as the downwardly-opening hole, is explained as an example. However, this may be also provided as a horizontally-opening hole or an upwardly-opening hole.

Moreover, it is also possible to provide barb parts (for example, the barb parts bulging in the right and left directions of FIG. 1) in the arrowhead part 27 of the microneedle 5.

Moreover, although the flow channels gradually become smaller from the medicinal solution supply needle side toward the microneedle side, it is also possible to become smaller smoothly in a taper shape.

Moreover, although the lower surfaces of the microneedles and the medicinal solution supply needles are flat, it is also possible to be in a shape with sharp ridge lines, so as to facilitate the puncturing.

Moreover, where the second divisional element 11 is bonded with the first divisional element 9 by heat welding, it is also possible to provide rib-shaped projections, on the outer peripheries of the microneedle side flow channels 19, the communication path 23 and the medicinal solution supply needle side flow channels 21, on the side of the bonding section 25 of the first divisional element 9. In this case, during heat welding, or during laser or ultrasonic welding, etc., the projections are melted, whereby the first divisional element 9 and the second divisional element 11 are bonded securely with each other, and further, the leakage of the medicinal solution out of the gap between the first divisional element 9 and the second divisional element 11 may also be prevented.

Moreover, in order to facilitate the alignment of the first divisional element 9 with the second divisional element 11, it is also possible to provide elements of which shapes engage with each other, such as holes and bosses, etc.

Moreover, with regard to the microneedle unit 101 and the injection device 111 according to the fourth embodiment, and also with regard to the microneedle unit 151 and the injection device 161 according to the fifth embodiment, it is also possible to provide a structure handling three or more medicinal solutions.

Moreover, with regard to the injection device 111 according to the fourth embodiment, it is also possible to depress and bias the depressing side seal members 121, 123, respectively by separate two pistons, so that two different types of the medicinal solutions can be discharged at different timings.

Moreover, in the fifth embodiment, various shapes can be applied to the mixing chamber 153. For example, it is also possible to provide minute shapes in the mixing chamber 153, so that two types of the medicinal solutions can be mixed efficiently.

Moreover, in the fifth embodiment, it is also possible that the flow channels confluent together without providing the mixing chamber 153.

Moreover, in the fifth embodiment, the diameter of the mixing chamber 153 ($d_1$) is set to be larger than the width of the medicinal solution supply needle side flow channel 21 ($W_1$). However, it is also possible that the diameter of the mixing chamber 153 ($d_1$) is set not to be larger than the width of the medicinal solution supply needle side flow channel 21 ($W_1$). In this case, although the mixing facilitation effect of two types of the medicinal solutions 117, 119 will become lower, since the volume of the mixing chamber 153 becomes smaller, the volume of medicinal solution remaining in the microneedle unit 151 without being injected can be reduced, and accordingly, much more volume of medicinal solution can be injected.

In addition, the structures illustrated in the drawings are merely examples of the present invention.

INDUSTRIAL APPLICABILITY

The present invention relates to a microneedle unit for performing prevention and treatment of various diseases, for example by subcutaneous or intracutaneous administration of an objective substance such as medicinal agent, and an injection device in which such an microneedle unit is incorporated, and more specifically, relates to that, of which connection is facilitated by simplifying the structure on the side of supplying medicinal solution, and also that, which can perform injection effectively. For example, the present invention is suitable for the microneedle unit and the injection device for vaccine injection.

EXPLANATION OF REFERENCE NUMERALS AND SIGNS

1 Microneedle Unit
5 Microneedle
7 Medicinal Solution Supply Needle
9 First Divisional Element
11 Second Divisional Element
19 Microneedle Side Flow Channel
21 Medicinal Solution Supply Needle Side Flow Channel
23 Communication Path
25 Bonding Section (Bonding Surface)
27 Arrowhead Part
29 Arrowhead Part
33 Medicinal Solution Outlet
35 Medicinal Solution Inlet
41 Microneedle Unit
43 Barb part
51 Injection Device
55 Depressing Mechanism
101 Microneedle Unit
103 Communication Path
105 Communication Path
111 Injection Device
151 Microneedle Unit
153 Mixing Chamber
161 Injection Device

The invention claimed is:

1. A microneedle unit comprising:
a first divisional element including a first divisional element main body, a plurality of microneedle part first elements protruding from one side of the first divisional element main body, at least one medicinal solution supply needle part first element protruding from another side of the first divisional element main body opposite to the one side thereof and having a number less than a number of the plurality of microneedle part first elements, microneedle side flow channels respectively formed in the plurality of microneedle part first elements, at least one medicinal solution supply needle side flow channel formed in the at least one medicinal solution supply needle part first element, and communication path elements communicating the microneedle side flow channels and the at least one medicinal solution supply needle side flow channel; and
a second divisional element attached to the first divisional element, and including a second divisional element main body, a plurality of microneedle part second elements protruding from one side of the second divisional element main body, and at least one medicinal solution supply needle part second element protruding from another side of the second divisional element main body opposite to the one side thereof and having a number less than a number of the plurality of microneedle part second elements,
wherein the second divisional element covers the microneedle side flow channels, the at least one medicinal solution supply needle side flow channel, and the communication path elements such that a part of each of the microneedle side flow channels forms a first horizontally-opening hole as a medicinal solution outlet and a part of the at least one medicinal solution supply needle side flow channel forms a second horizontally-opening hole as a medicinal solution inlet, and
the second divisional element is bonded on the first divisional element such that the plurality of microneedle part first elements, the microneedle side flow channels, and the plurality of microneedle part second elements respectively form a plurality of microneedles, and the at least one medicinal solution supply needle part first element, the at least one medicinal solution supply needle side flow channel, and the at least one medicinal solution supply needle part second element form at least one medicinal solution supply needle having a number less than a number of the plurality of microneedles.

2. The microneedle unit as claimed in claim 1, wherein, the medicinal solution outlet is formed at an end of each of the plurality of microneedles.

3. The microneedle unit as claimed in claim 1, wherein, the at least one medicinal solution supply needle includes barb parts provided at an end thereof on the first divisional element.

4. The microneedle unit as claimed in claim 1, wherein, a lower surface of a section of the first divisional element constituting a part of one of the plurality of microneedles is flat.

5. The microneedle unit as claimed in claim 1, wherein, the second divisional element is in a form of a film, a sheet or a tape.

6. The microneedle unit as claimed in claim 1, wherein, external dimensions of the second divisional element are smaller than external dimensions of the first divisional element.

7. The microneedle unit as claimed in claim 1, wherein, the at least one medicinal solution supply needle includes a plurality of medicinal solution supply needles with medicinal solution supply needle side flow channels, and the plurality of microneedles is sorted into groups so that the microneedles in each group and one medicinal solution supply needle of the plurality of medicinal solution supply needles constitute one set, and the microneedle side flow channels, the medicinal solution supply needle side flow channels, and the communication path elements are compartmented by each set.

8. The microneedle unit as claimed in claim 1, wherein, the at least one medicinal solution supply needle includes a plurality of medicinal solution supply needles with medicinal solution supply needle side flow channels, and the medicinal solution supply needle side flow channels of the plurality of medicinal solution supply needles are consolidated into one mixing chamber, and the mixing chamber is communicating with the microneedle side flow channels of the plurality of microneedles.

9. The microneedle unit as claimed in claim 1, wherein a surface of the first divisional element is a flat surface, and the microneedle side flow channels of the plurality of microneedles and the at least one medicinal solution supply needle side flow channel of the at least one medicinal solution supply needle are grooves dented from the flat surface.

10. The microneedle unit as claimed in claim 9, wherein the second divisional element is fixed to the flat surface of the first divisional element and covers the grooves such that two ends of the grooves are not covered by the second divisional element to thereby form the medicinal solution inlet and the medicinal solution outlet.

11. The microneedle unit as claimed in claim 1, wherein each of the plurality of microneedles includes an arrowhead part on an end of the first divisional element.

12. The microneedle unit as claimed in claim 11, wherein the first divisional element includes a divisional surface contacting the second divisional element, and a thickness of the second divisional element is set not to be larger than a height of the arrowhead part protruding from the divisional surface of the first divisional element.

13. The microneedle unit as claimed in claim 11, wherein a chamfered part is formed on an end of the second divisional element, which is located adjacent to the arrowhead part of the first divisional element.

14. The microneedle unit as claimed in claim 1, wherein, the first divisional element main body includes arrowhead parts at a tip end on one side of the first divisional element main body, and the medicinal solution outlet is arranged adjacent to each of the arrowhead parts.

15. The microneedle unit as claimed in claim 14, wherein, the second divisional element has a thickness less than a horizontal protrusion of the arrowhead portion from a boding surface of the first divisional element and the second divisional element.

16. The microneedle unit as claimed in claim 1, wherein, each of the plurality of microneedle part first elements includes a first arrowhead part at one end thereof, and each of the plurality of microneedle part second elements includes a second arrowhead part at one end thereof opposite to the one end of each of the plurality of microneedle part first elements, and the second divisional element is arranged to be offset on the first divisional element to form the first horizontally-opening hole opened in a direction perpendicular to a protrusion of each of the plurality of microneedle part first elements between one end of the second divisional element and the first arrowhead part, and to form the second horizontally-opening hole opened in a direction perpendicular to a protrusion of each of the plurality of microneedle part second elements between another end of the second divisional element opposite to the one end thereof and the second arrowhead part.

17. An injection device, comprising:
the microneedle unit as claimed in claim 1, which is set in a flattened shape expanding in an alignment direction of the plurality of microneedles of the microneedle unit.

18. The injection device as claimed in claim 17, wherein, the plurality of microneedles is set so as to offset from a center of the injection device.

19. The injection device as claimed in claim 17, further comprising
a seal member; and
a medicinal solution retaining part sealed by the seal member,
wherein with penetration of the at least one medicinal solution supply needle through the seal member, a medicinal solution in the medicinal solution retaining part is delivered to the plurality of microneedles via the at least one medicinal solution supply needle.

20. The injection device as claimed in claim 19, further comprising
a needle cap covering the plurality of microneedles,
wherein with depressing of the needle cap, the at least one medicinal solution supply needle penetrates through the seal member.

21. The injection device as claimed in claim 19, further comprising
a depressing mechanism provided so as to extract air from the medicinal solution retaining part.

22. The injection device as claimed in claim 21, further comprising
a locking mechanism provided so as to lock the depressing mechanism,
wherein with release of the locking mechanism, the depressing mechanism discharges the medicinal solution from the medicinal solution outlet.

23. The injection device as claimed in claim 19, wherein, the medicinal solution retaining part includes a plurality of retaining parts.

24. The injection device as claimed in claim 23, wherein
the at least one medicinal solution supply needle includes a plurality of medicinal solution supply needles with medicinal solution supply needle side flow channels, and the plurality of microneedles is sorted into groups so that the microneedles in each group and one medicinal solution supply needle of the plurality of medicinal solution supply needles constitute one set, and the microneedle side flow channels, the medicinal solution supply needle side flow channels, and the communication path elements are compartmented by each set;
different medicinal solutions are retained, respectively, in the plurality of retaining parts; and
the plurality of medicinal solution supply needles corresponds to the plurality of retaining parts.

25. The inoculation device as claimed in claim 23, wherein
the at least medicinal solution supply needles needle includes a plurality of medicinal solution supply needles with medicinal solution supply needle side flow channels, and the medicinal solution supply needle side flow channels of the plurality of medicinal solution supply needles are consolidated into one mixing chamber, and the mixing chamber is communicating with the microneedle side flow channels of the plurality of microneedles;
different medicinal solutions are retained, respectively, in the plurality of retaining parts; and
the plurality of medicinal solution supply needles corresponds to the plurality of retaining parts.

* * * * *